US006806363B1

(12) United States Patent
Collins et al.

(10) Patent No.: US 6,806,363 B1
(45) Date of Patent: Oct. 19, 2004

(54) COBALAMIN CONJUGATES USEFUL AS ANTITUMOR AGENTS

(75) Inventors: Douglas A. Collins, Rochester, MN (US); Henricus P. C. Hogenkamp, Roseville, MN (US)

(73) Assignees: Mayo Foundation for Medical Education & Research, Rochester, MN (US); Minnesota, Regents of the University, Minneapolis, MN (US)

( * ) Notice: Subject to any disclaimer, the term of this patent is extended or adjusted under 35 U.S.C. 154(b) by 0 days.

(21) Appl. No.: 09/690,197

(22) Filed: Oct. 16, 2000

Related U.S. Application Data

(60) Provisional application No. 60/159,873, filed on Oct. 15, 1999, and provisional application No. 60/129,733, filed on Apr. 16, 1999.

(51) Int. Cl.$^7$ ............................................. C07H 23/00
(52) U.S. Cl. ...................... 536/26.4; 514/52; 514/64; 536/26.41; 536/26.44; 536/26.6; 424/1.73
(58) Field of Search .................. 514/52, 64; 536/26.4, 536/26.41, 26.44, 26.6, 25; 424/1.73

(56) References Cited

U.S. PATENT DOCUMENTS

| | | | |
|---|---|---|---|
| 3,936,440 A | 2/1976 | Nath | 260/211.7 |
| 3,981,863 A | 9/1976 | Niswender et al. | 536/25 |
| 4,209,614 A | 6/1980 | Bernstein et al. | 536/25 |
| 4,279,859 A | 7/1981 | Gutcho et al. | 422/61 |
| 4,283,342 A | 8/1981 | Yollees | 260/345.1 |
| 4,301,140 A | 11/1981 | Frank et al. | 424/1.5 |
| 4,465,775 A | 8/1984 | Houts | 436/503 |
| 4,612,302 A | 9/1986 | Szabo et al. | 514/11 |
| 4,684,620 A | 8/1987 | Hruby et al. | 514/11 |
| 4,853,371 A | 8/1989 | Coy et al. | 514/12 |
| 5,308,606 A | 5/1994 | Wilson et al. | 424/1.65 |
| 5,405,839 A | 4/1995 | Toraya et al. | 514/52 |
| 5,428,023 A | 6/1995 | Russell-Jones et al. | 514/21 |
| 5,449,720 A | 9/1995 | Russell-Jones et al. | 525/54.1 |
| 5,462,724 A | 10/1995 | Schinazi et al. | 424/1.77 |
| 5,548,064 A | 8/1996 | Russell-Jones et al. | 530/380 |
| 5,574,018 A | 11/1996 | Habberfield et al. | 514/21 |
| 5,589,463 A | 12/1996 | Russell-Jones et al. | 514/21 |
| 5,599,796 A | 2/1997 | Schinazi et al. | 514/44 |
| 5,608,060 A | 3/1997 | Axworthy et al. | 540/474 |
| 5,739,313 A | 4/1998 | Collins et al. | 536/26.44 |
| 5,807,832 A | 9/1998 | Russell-Jones et al. | 514/21 |
| 5,840,880 A | 11/1998 | Morgan et al. | 536/26.4 |
| 5,869,465 A | 2/1999 | Morgan et al. | 514/52 |
| 5,869,466 A | 2/1999 | Russell-Jones et al. | 514/52 |
| 5,872,107 A | 2/1999 | Schinazi et al. | 514/44 |
| 5,877,165 A | 3/1999 | Miura | 514/64 |
| 5,936,082 A | 8/1999 | Bauer | 540/145 |
| 6,004,533 A | 12/1999 | Collins et al. | 424/1.73 |
| 6,074,625 A | 6/2000 | Hawthorne et al. | 424/1.11 |
| 6,083,926 A | 7/2000 | Morgan et al. | 514/52 |
| 6,096,290 A | 8/2000 | Collins et al. | 424/1.65 |
| 6,150,341 A | 11/2000 | Russell-Jones et al. | 514/52 |
| 6,180,766 B1 | 1/2001 | Schinazi et al. | 536/22.1 |
| 6,211,355 B1 | 4/2001 | Collins et al. | 536/26.41 |
| 6,262,253 B1 | 7/2001 | Russell-Jones et al. | 536/26.41 |
| 6,315,978 B1 | 11/2001 | Grissom et al. | 424/1.53 |

FOREIGN PATENT DOCUMENTS

| | | |
|---|---|---|
| EP | 0 005 834 | 12/1979 |
| EP | 0 069450 | 1/1983 |
| EP | 0 165 716 | 12/1985 |
| WO | WO 89/01475 | 2/1989 |
| WO | WO 92/13571 | 8/1992 |
| WO | WO 94/27613 | 12/1994 |
| WO | WO 94/27641 | 12/1994 |
| WO | WO 95/27723 | 10/1995 |
| WO | WO 96/31243 | 10/1996 |
| WO | WO 97/14711 | 4/1997 |
| WO | WO 97/18231 | 5/1997 |
| WO | WO 97/33627 | 9/1997 |
| WO | WO 98/08859 | 3/1998 |
| WO | WO 99/65930 | 12/1999 |
| WO | WO 00/62808 | 10/2000 |
| WO | WO 00/74721 | 12/2000 |
| WO | WO 01/30967 | 5/2001 |

OTHER PUBLICATIONS

Primus, Bioconjugate Chemistry 7, 532–535, 1996.*
Amagasaki et al., *Blood*, 76:7, 1380–1386, (1990).
Anton et al., *The J. of Biol. Chem.* 255:10 of May 25, pp. 4507–4510 (1980).
Begly et al., *J. Cell Physiol.*, 156, 43–47 (1993).
Blomquist et al., *Experientia*, 25, 294–296 (1969).
Cooper et al., *Nature*, 191, 393–395 (1961).
Collins et al., *Mayo Clinic Proc.*, 74, 687–691 (1999).
Collins et al., *J. Nucl. Med.*, 38:5, 717–723 (1997).
Flodh et al., *Int. J. Cancer*: 3, 694–699 (1968).
Hogenkamp et al., *Biochemistry*, 13:13, 2736–2739 (1974).
Hogenkamp, et al. *Nucl. Med. and Biol.*, 27, 89–92 (2000).
Lindemans, et al., *Experimental Cell Research*, 184:2, Oct. 1989.
Smeltzer, et al., Synthesis and Characterization of Fluorescent Cobalamin (CobalaFluor) Derivatives for Imaging, *Organic Letters*, vol. 3, No. 6, pp. 799–801, (2001).
U.S. patent application Ser. No. 09/690,198, Collins et al., filed Oct. 16, 2000.
U.S. patent application Ser. No. 09/626,213, Collins et al., filed Oct. 16, 2001.
U.S. patent application Ser. No. 09/690,353, Collins et al., filed Oct. 16, 2001.

(List continued on next page.)

*Primary Examiner*—Christopher S. F. Low
*Assistant Examiner*—David Lukton
(74) *Attorney, Agent, or Firm*—Sherry M. Knowles; King & Spalding, LLP

(57) ABSTRACT

The invention provides cobalamin compounds linked to a neutron capture therapy target (e.g. Boron-10 or Gadolinium-157), and optionally linked to a detectable moiety, as well as pharmaceutical compositions comprising the compounds, and methods for using the compounds in medical diagnosis and therapy.

57 Claims, 3 Drawing Sheets

OTHER PUBLICATIONS

U.S. patent application Ser. No. 09/873,142, Collins et al., filed May 31, 2001.
U.S. patent application Ser. No. 09/873,164, Collins et al., filed May 31, 2001.
U.S. patent application Ser. No. 10/028,857, Collins et al., filed Oct. 25, 2001.
U.S. patent application Ser. No. 10/027,593, Collins et al., filed Oct. 25, 2001.
Wilbur, et al., "Biotin Reagents for Antibody Pretargeting. 4. Selection of Biotin Conjugates for in Vivo Application Based on Their Dissociation Rate from Avidin and Streptavidin." *Bioconjugate Chem.*, 11(4), 569–583 (Jun. 29, 2000).
Wilbur, et al., "Evaluation of Biotin–Dye Conjugates for Use in an HPLC Assay to Assess Relative Binding of Biotin Derivatives with Avidin and Streptavidin." *Bioconjugate Chem.*, 11(4), 584–598 (Jun. 29, 2000).
Finkler et al., *Arch. Biochem. Biophys.*, 120, 79–85 (1967).
Hall et al., *J. Cell Physiol.*, 133, 187–191 (1987).
Rappazzo, et al., *J. Clin. Invest.*, 51, 1915–1918 (Jul. 1972).
Ruser, et al., *Bioconjugate Chem.*, vol. 1, 345–349 (1990).
Virzi, et al. *Nucl. Med. Biol.*, vol. 19, No. L, pp. 239–244 (1992).

* cited by examiner

COBALAMIN CONJUGATES USEFUL AS ANTITUMOR AGENTS

RELATED APPLICATION

The present application claims priority under 35 U.S.C. 119(e) to U.S. Provisional Patent Application No. 60/159,873, filed Oct. 15, 1999, and under 35 U.S.C. 120 to International Application No. PCT/US00/10100, filed Apr. 15, 2000, designating the United States, which claims priority to U.S. Provisional Application No. 60/129,733, filed Apr. 16, 1999.

BACKGROUND OF THE INVENTION

Boron neutron capture therapy is based on the nuclear reaction that occurs when a stable isotope, $^{10}$B, is irradiated with low energy (0.025 eV) or thermal neutrons to yield helium nuclei (α-particles) and $^{7}$Li nuclei.

The therapeutic potential of this reaction was recognized by Locher over 50 years ago (Locher, G. L. et al., *Am. J. Roentgenol. Radium Ther.*, 36 1–13 (1936)), but it was Sweet (Javid, M. et al., *J. Clin. Invest.*, 31, 603–610 (1952); Sweet, W. H., *N. Engl. J. Med.*, 245, 875–878 (195 1); Sweet, W. H. et al., *J. Neurosurg.*, 9, 200–209 (1952)), who first suggested that boron neutron capture therapy (BNCT) might be useful for the treatment of brain tumors.

Shortly thereafter, a clinical trial was initiated at the Brookhaven National Laboratory in cooperation with Sweet and others at the Massachusetts General Hospital utilizing borax as the capture agent (Farr, L. E. et al., *Am. J. Roentgenol.*, 71, 279–291 (1954); Godwin, J. T. et al., *Cancer (Phila.)*, 601–615 (1955)). The objective at that time was to use BNCT as an adjunct to surgery for the treatment of patients with the most highly malignant and therapeutically refractory of all brain tumors, glioblastoma multiforme.

Further trials were carried out in the early 1960s, but these failed to show any evidence of therapeutic efficacy (Farr, L. E. et al., supra; Godwin, J. T. et al., supra; Asbury, A. K. et al., *J. Neuropathol. Exp. Neurol.*, 31, 278–303 (1972)) and were associated with adverse effects in normal tissues (Asbury, A. K. et al., supra). Stimulated by the more encouraging clinical studies of Hatanaka et al. (Hatanaka, H. A., *J. Neurol.*, 209, 81–94(1975); Hatanaka, H. et al., *Boron Neutron Capture Therapy for Tumors*, Chap. 25, pp. 349–378. Niigata, Japan: Nishimura Co., Ltd. (1986)) for the treatment of malignant gliomas and those of Mishima et al. (Mishima, Y. et al., *Lancet.*, 2, 388–289 (1989)) for melanoma, there has been renewed national and international interest in BNCT.

The theoretical advantage of BNCT is that it is a two component or binary system, consisting of $^{10}$B and thermal neutrons, which when combined together generate high linear energy transfer (LET) radiation capable of selectively destroying tumor cells without significant damage to normal tissues. In order for BNCT to succeed a critical amount of $^{10}$B and a sufficient number of thermal neutrons must be delivered to individual tumor cells.

Over the past few years the Department of Energy and the NIH have renewed funding for BNCT-related research, and this has supported a growing number of investigators in many different disciplines. Advances in BNCT in the areas of compound distribution and pharmacokinetics compare favorably with other emerging modalities such as photon activation therapy, photodynamic therapy, and the use of radiolabeled antibodies for cancer treatment in which physiological targeting is used.

There are a number of nuclides that have a high propensity for absorbing low energy or thermal neutrons, and this property, referred to as the neutron capture cross-section (σ), is measured in barns (1 b=10$^{-24}$ cm$^2$). Of the various nuclides that have high neutron capture cross-sections, $^{10}$B is the most attractive for the following reasons: (a) it is nonradioactive and readily available, comprising approximately 20% of naturally occurring boron: (b) the particles emitted by the capture reaction [$^{10}$B(n,α)$^{7}$Li] are largely high LET: (c) their path lengths are approximately 1 cell diameter (10–14 μm), theoretically limiting the radiation effect to those tumor cells that have taken up a sufficient amount of $^{10}$B and simultaneously sparing normal cells and (d) the extensive chemistry of boron is such that it can be incorporated into a multitude of different chemical structures.

$^{7}$Li and α-particles are the primary fission product of the neutron capture reaction with $^{10}$B. α-Particles are relatively slow and give rise to closely spaced ionizing events that consist of tracks of sharply defined columns. They have a path length of approximately 10 μm, are high LET, and destroy a wide variety of biologically active molecules including DNA, RNA, and proteins. For these reasons there is little, if any, cellular repair from α-particle-induced radiation injury.

Since the $^{10}$B(n,α)$^{7}$Li reaction will produce a significant biological effect only when there is a sufficient fluence of thermal neutrons and a critical amount of $^{10}$B localized around, on, or within the cell, the radiation produced can be extremely localized thereby sparing normal tissue components. Thus, selectivity is simultaneously one of the advantages and disadvantages of BNCT, since it requires delivery of boron-10 to tumor cells in greater amounts than normal cells.

Ideally, boron compounds to be used for BNCT should have a high specificity for malignant cells with concomitantly low concentrations in adjacent normal tissues and blood. Since it is desirable to confine the radiation solely to these cells, an intracellular and optimally intranuclear localization of boron would be preferred.

Several boron-containing derivatives of chlorpromazine have been synthesized (Nakagawa, T. et al., *Chem. Pharm. Bull. (Tokyo)*, 24, 778–781 (1976); Alam, F. et al., *Sthralenter. Onkol.*, 165, 121–125 (1989)) and are being evaluated for their in vivo tumor localizing properties. p-Boronophenylalanine is another compound that is being studied as a potential capture agent for the treatment of melanoma. The rationale for its use is the avidity of melanomas for aromatic amino acids and their subsequent incorporation into melanin (Ichihashi, M. et al., *J. Invest. Dermatol.*, 78, 215–218 (1982); Mishima, Y. et al., *Neutral Capture Therapy*, 230–236, Niigata, Japan: Nishimura Co., Ltd. (1986)).

Tumor localization has been demonstrated following I.V. administration by means of whole body autoradiography (Coderre, J. A. et al., *Cancer Res.*, 48, 6313–6316 (1988)) and in several patients with cutaneous melanoma following perilesional injection (Mishirna, Y. et al., *Sthralenther. Onkol.*, 165, 251–254 (1989)). Stimulated by Mishima's experience, a number of other boron-containing amino acids have been synthesized that potentially could be incorporated in larger amounts into proteins of malignant cells (Hall, I. H. et al., *J. Pharm. Sci.*, 68, 685–688 (1979).

Another approach to the selective targeting of boron to melanomas is based on the observation that thiouracil is preferentially incorporated into melanotic melanomas during melanogenesis (Whittacker, J. R., *J. Biol. Chem.*, 246, 6217–6226(1971)). This observation provided the impetus for the synthesis of several boron-containing thiouracils (Gabel, D., *Clinical Aspects of Neutron Capture Therapy*, 233–241, New York: Plenum Publishing Co. (1989)), and these currently are being evaluated in animals.

Two other classes of compounds with a propensity for localizing in malignant tumors are the porphyrins and the related phthalocyanines. The biochemical basis by which these compounds achieve elevated concentration in malignant tumors is unknown, but this observation has served as the rationale for the use of hematoporphyrin derivative in the photodynamic therapy of cancer (Dougherty, T. J. et al., *Porphyrin Photosensitization*, 3–13, New York: Plenum Publishing Corp. (1981)).

The high concentration of these compounds in tumors and their intracellular localization and persistence have stimulated several groups of investigators to synthesize boronated pokphyrins (Kahi, S. B. et al., *Neutron Capture Therap*, 61–67, Niigata, Japan: Nishimura Co., Ltd. (1986)) and phthalocyanines (Alam, F. et al, *Strahlenther. Oncol.*, 165, 121–123 (1989)) as potential capture agents. Boronated porphyrins appear to be 3–4 times more effective per unit dose in cell culture than the monomeric or dimeric form of $Na_2B_{12}H_{11}SH$ (Laster, B. H. et al., *Strahlenther. Oncol.*, 165, 203–205 (1989)). Although liver concentrations of these compounds are also high (Kahl, S. B. et al., supra) this would not limit their use as a capture agent for the treatment of brain tumors.

One final category of low molecular weight boron compounds are boron-containing purines and pyrimidines and their nucleosides. The rationale for their development is that such compounds may be selectively incorporated into rapidly proliferating tumor cells and trapped within the cell following their conversion to the corresponding nucleotide. Alternatively, these bases and their nucleosides may function as analogues of naturally occurring precursors of nucleic acids and become incorporated into nuclear DNA.

Cytoplasmic or preferably a nuclear localization of all of these boron compounds would be advantageous since the heavy particles resulting from the capture reaction would deliver a greater proportion of their energy to intranuclear targets, thereby permitting lower boron concentrations than would have been required if the compounds were located extracellularly (Gabel, D. et al., *Radiat. Res.*, 111, 14–25 (1987); Fairchild, R. G. et al., *Int. J. Radiat. Oncol. Biol. Phys.*, 11, 831–840 (1985)). Schinazi and Prusoff(Schinazi, R. F. et al., *Tetrahedron Lett.*, 50, 4981–4984 (1978)) have synthesized the first born containing nucleoside, 5-dihydroloxyboryl-2'-deoxyuridine, an analogue of thymidine, and have shown that it was not cytotoxic to African green monkey (Vero) cells at a concentration level of 1600 μM (Laster, B. H. et al., *Neutron Capture Therapy*, 46–54, Niigata, Japan: Nishimura Co., Ltd. (1986)). In vitro neutron radiation studies of cells grown in the presence of 5-dihydroxy-2'-deoxyuridine produced a biological effect that was equivalent to a concentration of ~6 μg $^{10}$B/g, which, if attainable in vivo, would be sufficient for BNCT.

During the 1960s and early 1970s, interests developed in the potential use of polyclonal antibodies directed against tumor-associated antigens for the delivery of drugs and radioisotopes to tumors (Pressman, D. et al., *Cancer Res.*, 40, 3001–3007 (1957); Ghose, T. et al., *Br. Med. J.*, 1, 90–93 (1967); Ghose, T. et al, *Cancer (Phila)*, 29, 1398–1400 (1972)). In 1964, Soloway suggested that antibodies might be used for the selective targeting of $^{10}$B to tumors (Soloway, A. H., supra). Hawthorne et al. (Hawthorne, M. F. et al., *J. Medicinal Chem.*, 15, 449–452(1972)) reported on the incorporation of the diazonium salt from 1-(4-aminophenyl)-1,2-dicarbo-closo-dodecaborane into antibodies directed against bovine serum albumin and polyclonal antibodies directed against human and mouse histocompatability antigens (Hawthorne, M. F. et al., supra).

It was claimed from in vitro experiments that these immunoconjugates were capable of delivering enough boron to human and murine lymphocytes to sustain a lethal $^{10}$B (n,α)$^7$Li reaction, as evidenced by reduced viability following neutron irradiation. However, the immunoconjugates contained only 0.2% natural boron by weight, which was equal to 6 atoms of $^{10}$B/molecule of antibody. In retrospect, it appears that there must have been some other explanation for the reduced cell viability that was observed. Sneath, et al. (Sneath, R. L., Jr., *J. Medicinal Chem.*, 17, 796–799 (1974)) showed that water-solubilizing groups had to be incorporated into protein-binding polyhedral boranes if protein solubility in aqueous systems was to be maintained.

Subsequently, a group of polyhedral borane derivatives containing protein-binding functional groups were linked to IgG molecules by means of the carbodiimide reaction without evidence of precipitation (Sneath, R. L. et al., *J. Medicinal Chem.*, 19, 1290–1294 (1976)).

One final category of macromolecular species that are possibly useful for the delivery of $^{10}$B is what may be termed "encapsulating complexes," such as liposomes, microspheres, and low density lipoproteins (Kahl, S. B. et al., *Strahlenther. Onkol.*, 165, 137–139 (1989)). Theoretically, large amounts of $^{10}$B could be encapsulated, and if these encapsulating complexes could be targeted to the tumor by linkage to a monoclonal antibody using existing methodology or targeting an endogenously expressed cell surface receptor, they might be powerful delivery systems. Again, there may be preferential localization in the reticuloendothelial system, and methodology would have to be developed to minimize this and maximize tumor uptake.

Cobalamin

For several years after the isolation of vitamin $B_{12}$ as cyanocobalamin in 1948, it was assumed that cyanocobalamin and possibly hydroxocobalamin, its photolytic breakdown product, occurred in man. Since then it has been recognized that cyanocobalamin is an artifact of the isolation of vitamin $B_{12}$ and that hydroxocobalamin and the two coenzyme forms, methylcobalamin and adenosylcobalamin, are the naturally occurring forms of the vitamin.

The structure of these various forms is shown in FIG. 1, wherein X is CN, OH, $CH_3$ or adenosyl, respectively. Hereinafter, the term cobalamin will be used to refer to all of the molecule except the X group. The fundamental ring system without cobalt (Co) or side chains is called corrin and the octadehydrocorrin is called corrole. FIG. 1 is adapted from *The Merck Index*, Merck & Co. (11th ed. 1989), wherein X is above the plane defined by the corrin ring and nucleotide is below the plane of the ring. The corrin ring has attached six amidoalkyl ($H_2NC(O)Alk$) substituents, at the 2, 3, 7, 8, 13, and 18 positions, which can be designated a–e and g, respectively. See D. L. Anton et al., *J. Amer. Chem. Soc.*, 102, 2215 (1980).

Methylcobalamin serves as the cytoplasmic coenzyme for $^5$N-methyltetrahydrofolate: homocysteine methyl transferase (methionine synthase, EC 2.1.1.13), which catalyzes the formation of methionine from homocysteine. Adenosylcobalamin is the mitochondrial coenzyme for methylmalonyl CoA mutase (EC5.4.99.2) which interconverts methylmalonyl CoA and succinyl CoA.

All forms of vitamin $B_{12}$ (adenosyl-, cyano-, hydroxo-, or methylcobalamin) must be bound by the transport proteins, Intrinsic Factor and Transcobalamin II to be biologically active. Specifically, gastrointestinal absorption of vitamin $B_{12}$ relies upon the intrinsic factor-vitamin $B_{12}$ complex being bound by the intrinsic factor receptors in the terminal ileum. Likewise, intravascular transpot and subsequent cellular uptake of vitamin $B_{12}$ throughout the body is dependent upon transcobalamin II and the cell membrane transcobalamin II receptors, respectively. After the transcobalamin II-vitamnin $B_{12}$ complex has been internalised, the transport protein undergoes lysozymal degradation, which releases vitamin $B_{12}$ into the cytoplasm. All forms of vitamin $B_{12}$ can then be interconverted into adenosyl-, hydroxo-, or methylcobalamin depending upon cellular demand. See, for example, A. E. Finkler et al., *Arch. Biochem. Biophys.*, 120, 79 (1967); C. Hall et al., *J. Cell Physiol.*, 133, 187 (1987); M. E. Rappazzo et al., *J. Clin. Invest.*, 51, 1915 (1972) and R. Soda et al., *Blood*, 65, 795 (1985).

Cells undergoing rapid proliferation have been shown to have increased uptake of thymidine and methionine. (See, for example, M. E. van Eijkeren et al., *Acta Oncologica*, 31, 539 (1992); K. Kobota et al., *J. Nucl. Med.*, 32, 2118 (1991) and K. Higashi et al., *J. Nucl. Med.*, 34, 773 (1993)). Since methylcobalamin is directly involved with methionine synthesis and indirectly involved in the synthesis of thymidylate and DNA, it is not surprising that methylcobalamin as well as Cobalt-57-cyanocobalamin have also been shown to have increased uptake in rapidly dividing tissue (for example, see, B. A Cooper et al., *Nature*, 191, 393(1961); H. Flodh, *Acta Radiol. Suppl.*, 4, 55 (1968); L. Bloomquist et al., *Experientia*,25,294 (1969)). Additionally, up-regulation in the number of transcobalamin II receptors has been demonstrated in several malignant cell lines during their accelerated thymidine incorporation and DNA synthesis (see, J. Lindemans et al., *Exp. Cell. Res.*, 184, 449 (1989); T. Amagasaki et al., *Blood*, 26, 138(1990) and J. A. Begly et al., *J. Cell Physiol.*, 156, 43 (1993).

Vitamin $B_{12}$ has several characteristics which potentially make it an attractive in vivo tumor therapeutic agent Vitamnin $B_{12}$ is water soluble, has no known toxicity, and in excess is excreted by glomerular filtration. In addition, the uptake of vitamin $B_{12}$ could potentially be manipulated by the administration of nitrous oxide and other pharmacological agents (D. Swanson et al., *Pharmaceuticals in Medical Imaging*, MacMillan Pub. Co., New York (1990) at pages 621–628).

A process for preparing $^{125}$I-vitamin $B_{12}$ derivatives is described in U.S. Pat. No. 3,981,863 issued to Niswender et al. In this process, vitamin $B_{12}$ is first subjected to mild hydrolysis to form a mixture of monocarboxylic acids, which Houts, infra disclosed to contain mostly the (e)-isomer. The mixture is then reacted with a p-(aminoalkyl) phenol to introduce a phenol group into the $B_{12}$ acids (via reaction with one of the free carboxylic acid groups). The mixed substituent $B_{12}$ derivatives are then iodinated in the phenol-group substituent. This U.S. patent teaches that the mixed $^{125}$I-$B_{12}$ derivatives so made are useful in the radioimmunoassay of $B_{12}$, using antibodies raised against the mixture.

U.S. Pat. No. 4,465,775 issued to T. M. Houts reported that the components of the radiolabeled mixture of Niswender et al. did not bind with equal affinity to IF. Houts disclosed that radioiodinated derivatives of the pure monocarboxylic (d)-isomer are useful in assays of $B_{12}$ in which IF is used. However, although Houts generally discloses that the monocarboxylic (d)-isomer can be labeled with fluorophores or enzymes and used in competitive assays for vitamin $B_{12}$ in fluids, a continuing need exists for labeled vitamin $B_{12}$ derivatives suitable for tumor and organ imaging and therapy.

U.S. Pat. No. 5,739,313 issued to Collins and Hogenkamp reported that cobalamin analogs comprising a linking group and a chelating group optionally comprising a detectable radionuclide or a paramagnetic ion localize in tumor cells and are useful for imaging tumors.

Despite previous efforts to identify a neutron capture agent that localizes in tumor cells in high concentration and is useful to treat cancer, there is currently a need for neutron capture agents that are useful to treat tumors.

SUMMARY OF THE INVENTION

The invention provides a compound of the invention which is a residue of a compound of formula I (FIG. 1) I linked to a residue of a molecule comprising Boron-10 (i.e., B-10), wherein X is CN, OH, $CH_3$, adenosyl, or a molecule comprising B-10; or a pharmaceutically acceptable salt thereof.

The invention also provides a compound wherein a residue of a compound of formula I (FIG. 1) is linked to a group of the formula Q—L—W—Det; wherein X is CN, OH, $CH_3$, adenosyl, a molecule comprising B-10, or Q—L—W—Det; wherein Det is a chelating group comprising Gd-157; L is a linker or absent; and W and Q are each independently —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or ($C_1$–$C_6$)alkyl; or a pharmaceutically acceptable salt thereof.

The invention also provides a compound wherein a residue of a compound of formula I (FIG. 1) is linked to a residue of a molecule comprising B-10; wherein a residue of the compound of formula I is also linked to a group of the formula Q—L—W—Det, wherein X is CN, OH, $CH_3$, adenosyl, a group of the formula Q—L—W—Det, or a molecule comprising B-10; wherein: Det is a chelating group comprising a therapeutic radionuclide or a diagnostic radionuclide; L is a linker or absent; and Q and W are each independently —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or ($C_1$–$C_6$)alkyl; or a pharmaceutically acceptable salt thereof.

The invention also provides a compound wherein a residue of a compound of formula I (FIG. 1) is linked to a residue of a molecule comprising B-10; wherein the residue of the compound of formula I is also linked to a group of the formula Q—L—W—Det, wherein X is CN, OH, $CH_3$, adenosyl, a group of the formula Q—L—W—Det or a molecule comprising B-10; Det is a chelating group comprising Gd-157; L is a linker or absent; and Q and W are each independently —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or ($C_1$–$C_6$)allyl; or a pharmaceutically acceptable salt thereof The invention also provides a compound wherein a residue of a compound of formula I (FIG. 1) I linked to a detectable radionuclide and also linked to a residue of a molecule comprising Boron-10 (i.e., B-10), wherein X is CN, OH, $CH_3$, adenosyl, or a molecule comprising B-10; or a pharmaceutically acceptable salt thereof.

The invention also provides a compound wherein a residue of a compound of formula I (FIG. 1) is linked to a detectable radionuclide; and is also linked to a group comprising Gd-157; wherein X is CN, OH, CH$_3$, adenosyl, a molecule comprising B-10, or a group comprising Gd-157; or a pharmaceutically acceptable salt thereof. Specifically, the group comprising Gd-157 can have the formula Q—L—W—Det; wherein Det is a chelating group comprising Gd-157; L is a linker or absent; and W and Q are each independently —N(R)C(=O)—, —C(=O)N(R)—, —OC(=O)—, —C(=O)O—, —O—, —S—, —S(O)—, —S(O)$_2$—, C(=O)—, —N(R)—, or a direct bond; wherein each R is independently H or (C$_1$–C$_6$)alkyl.

The invention also provides a compound of wherein a residue of a compound of formula I (FIG. 1) is linked 1) to a molecule comprising B-10 or to a chelating group comprising Gd-157, and is linked 2) to at least one residue of the formula Q—L—W—Det; wherein each Det is independently a chelating group comprising a metallic radionuclide; each L is independently a linker or absent; and each W and Q is independently —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or (C$_1$–C$_6$)alkyl; or a pharmaceutically acceptable salt thereof.

The invention also provides a pharmaceutical composition comprising a compound of the present invention and a pharmaceutically acceptable carrier.

The invention also provides a method of treating a tumor in a mammal in need of such treatment comprising administering to the mammal an effective amount of a compound of the present invention; and administering neutron capture therapy.

The invention also provides a method for imaging a tumor in a mammal in need of such imaging comprising administering to the mammal a detectable amount of a compound of the present invention in combination with a pharmaceutically acceptable vehicle effective to image the tumor; and detecting the presence of the compound.

The invention also provides a compound of the present invention for use in medical therapy or diagnosis.

The invention also provides the use of a compound of the present invention for the manufacture of a medicament for imaging a tumor in a mammal (e.g., a human).

The invention also provides the use of a compound of the present invention for the manufacture of a medicament for treating a tumor in a mammal (e.g., a human).

The invention also provides intermediates disclosed herein that are useful in the preparation of the compounds of the present invention as well as synthetic methods useful for preparing the compounds of the invention

DETAILED DESCRIPTION OF THE INVENTION

Figure 1:
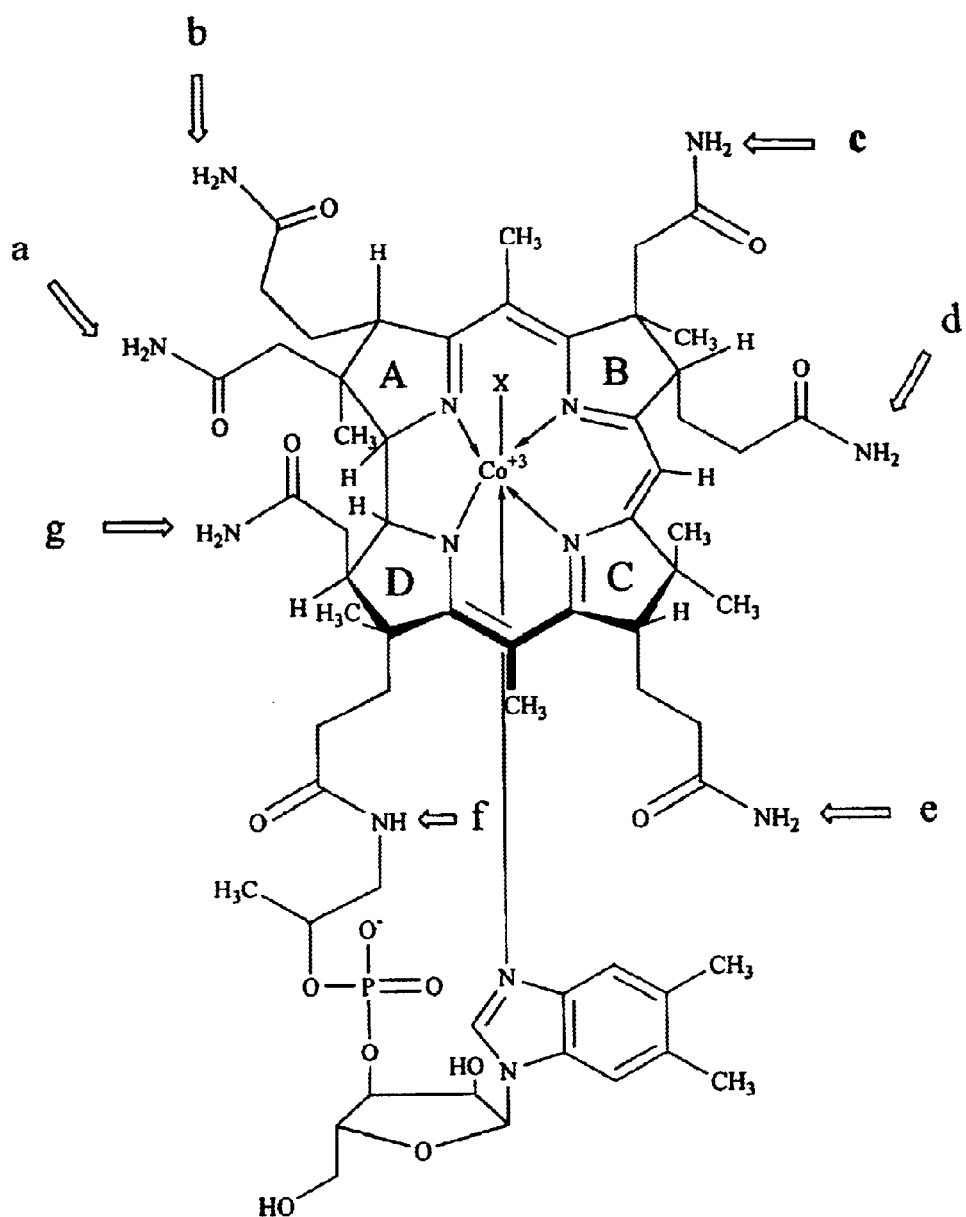
FIG. 1 depicts the structure of cobalamin wherein X is CN (cyano), OH, CH$_3$ or adenosyl.

Applicant has discovered certain cobalamin analogs are useful, in combination with neutron capture therapy, to treat tumors. Applicant has also discovered certain cobalamin analogs are useful as neutron capture agents and as tumor imaging agents.

The following definitions are used, unless otherwise described: halo is fluoro, chloro, bromo, or iodo. Alkyl, alkoxy, alkenyl, alkynyl, etc. Dent both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

Specific and preferred values listed below for radicals, substituents, and ranges, are for illustration only; they do not exclude other defined values or other values within defined ranges for the radicals and substituents.

It is appreciated that those skilled in the art will recognize that compounds of the present invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antitumor activity or utility as an antitumor imaging agent using the standard tests described herein, or using other similar tests which are well known in the art.

Specifically, (C$_1$–C$_{14}$)alkyl can be methyl, ethyl, propyl, isopropyl, butyl, iso-butyl, sec-butyl, pentyl, 3-pentyl, hexyl, heptyl, octyl, nonyl, decyl undecyl, dodecyl, tridecyl or tetradecyl.

Specifically, (C$_2$–C$_{14}$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4octenyl, 5-octenyl, 6-octenyl 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4tetradecenyl, 5-tetradecenyl, 6-tetradecenyl, 7-tetradecenyl, 8-tetradecenyl, 9-tetradecenyl, 10tetradecenyl, 11-tetradecenyl, 12-tetradecenyl or 13-tetradecenyl.

Specifically, (C$_2$–C$_{14}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl 4-hexynyl, 5-hexynyl, 1-heptynyl, 2-heptynyl, 3-heptynyl, 4-heptynyl, 5-heptynyl, 6heptynyl, 1-octynyl, 2-octynyl, 3-octynyl, 4octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2decynyl, 3-decynyl, 4-decynyl, 5-decynyl, 6decynyl, 7-decynyl, 8-decynyl, 9-decynyl, 1-undecynyl, 2-undecynyl, 3-undecynyl, 4-undecynyl, 5-undecynyl, 6-undecynyl, 7-undecynyl, 8-undecynyl, 9-undecynyl, 10-undecynyl, 1-dodecynyl, 2-dodecynyl, 3-dodecynyl, 4-dodecynyl, 5-dodecynyl, 6-dodecynyl, 7-dodecynyl, 8-dodecynyl, 9-dodecynyl, 10dodecynyl, 11-dodecynyl, 1-tridecynyl, 2-tridecynyl, 3-tridecynyl, 4-tridecynyl, 5-tridecynyl, 6-tridecynyl, 7-tridecynyl, 8-tridecynyl, 9-tridecynyl, 10-tridecynyl, 11-tridecynyl, 12-tridecynyl, 1-tetradecynyl, 2-tetradecynyl, 3-tetradecynyl, 4-tetradecynyl. 5-tetradecynyl, 6-tetradecynyl, 7-tetradecynyl, 8-tetradecynyl, 9-tetradecynyl, 10tetradecynyl, 11-tetradecynyl, 12-tetradecynyl or 13-tetradecynyl.

Specifically "aryl" can be phenyl, indenyl, or naphthyl.

Specifically ($C_3$–$C_8$)cycloalkyl can be cyclopropyl, cyclobutyl, cyclopentyl, cyclohexyl, cycloheptyl or cyclooctyl.

As used herein, an "amino acid" is a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; and tert-butylglycine) residue having one or more open valences. The term also comprises natural and unnatural amino acids bearing conventional amino protecting groups (e.g. acetyl, acyl, trifluomacetyl, or benzyloxycarbonyl), as well as natural and unnatural amino acids protected at carboxy (e.g. as a ($C_1$–$C_6$)alkyl, phenyl or benzyl ester or amide) with conventional protecting groups. Other suitable amino and carboxy protecting groups are known to those skilled in the art (See for example, T. W. Greene, *Protecting Groups In Organic Synthesis*; Wiley: New York, 1981; D. Voet, *Biochemistry*, Wiley: New York, 1990; L. Stryer, *Biochemistry*, (3rd Ed.), W. H. Freeman and Co.: New York, 1975; J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein). According to the invention, the amino or carboxy protecting group can also comprise a radionuclide (e.g., Fluorine-18, Iodine-123, or Iodine-124).

As used herein, a "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

Particular and specific values listed below for radicals, substituents, and ranges, are for illustration only and they do not exclude other defined values or other values within defined ranges for the radicals and substituents.

Specifically, the peptide can be poly-L-lysine, poly-L-glutamic acid, poly-L-aspartic acid, poly-L-histidine, poly-L-ornithine, poly-L-serine, poly-L-threonine, poly-L-tyrosine, poly-L-lysine-L-phenylalanine or poly-L-lysine-L-tyrosine.

As used herein, a "residue of a compound of formula I" is a radical of a compound of formula I having one or more open valences. Any synthetically feasible atom or atoms of the compound of formula I may be removed to provide the open valence, provided the resulting compound is able to localize in or near tumors. Based on the linkage that is desired, one skilled in the art can select suitably functionalized starting materials that can be derived from a compound of formula I using procedures that are known in the art. For example, suitable atoms that may be removed include the $NH_2$ group of the a-carboxamide (illustrated in FIG. 1) or a hydrogen atom from the $NH_2$ group of the a-carboxamide, the $NH_2$ group of the b-carboxamide (illustrated in FIG. 1) or a hydrogen atom from the $NH_2$ group of the b-carboxamide, the $NH_2$ group of the d-carboxamide (illustrated in FIG. 1) or a hydrogen atom from the $NH_2$ group of the d-carboxamide, the $NH_2$ group of the e-carboxamide (illustrated in FIG. 1) or a hydrogen atom from the $NH_2$ group of the e-carboxamide, and X at the 6-position (illustrated in FIG. 1). In addition, the hydrogen atom of the hydroxy group at the 3' position of the sugar, the hydrogen atom from the hydroxyl group at the 3' position of the sugar, the hydrogen atom of the $CH_2OH$ group at the 5' position, or the hydrogen atom from the hydroxyl group at the 5' position of the sugar ring may be removed.

As used herein, "adenosyl" is an adenosine radical in which any synthetically feasible atom or group of atoms have been removed, thereby providing an open valence. Synthetically feasible atoms which may be removed include the, hydrogen atom of the hydroxy group at the 5' position. Accordingly, adenosyl can conveniently be attached to the 6-position of a compound of formula I via the 5' position of adenosyl.

As used herein, a "molecule comprising B-10" can be any compound that contains at least one B-10 atom. The nature of the molecule that includes B-10 is not critical. The compound, however, must be nontoxic and must be able to enter the tumor cell or locate near the tumor cell when the molecule comprising B-10 is attached.

As used herein, a "residue of a molecule comprising B-10" is a radical of a molecule comprising B-10 having one or more open valences. Any synthetically feasible atom or atoms of the molecule comprising B-10 may be removed to provide the open valence, provided bioactivity is substantially retained. Based on the linkage that is desired, one skilled in the art can select suitably functionalized starting materials that can be derived from a molecule comprising B-10 using procedures that are known in the art.

As used herein, a "residue of o-carborane," a "residue of m-carborane," or a "residue of p-carborane" is a radical of o-carborane, m-carborane or p-carborane, respectively, having one or more open valences. Any synthetically feasible atom or atoms of o-carborane, m-carborane or p-carborane may be removed to provide the open valence, provided bioactivity is substantially retained. Based on the linkage that is desired, one skilled in the art can select suitably functionalized starting materials that can be derived from o-carborane, m-carborane or p-carborane using procedures that are known in the art.

Boron Compounds Useful for Neutron Capture Therapy

The invention provides a compound of formula I (FIG. 1) linked to one or more molecules comprising B-10, wherein X is CN, OH, CH$_3$, adenosyl or a molecule comprising B-10; or a pharmaceutically acceptable salt thereof.

A variety of molecules comprising B-10 known in the art are useful in the present invention. The molecules vary considerably in structure but are suitable to practice the present invention. Acceptable species include boron containing amino acids, carbohydrates, and nucleosides, as well as carboranes. A wide variety of boron-containing compounds are commercially available, or are known in the art. A variety of molecules comprising B-10 are commercially available from Boron Biologicals, Inc., Raleigh, N.C. and RysCor Science, Inc., Raleigh, N.C.

Specifically, at least one molecule comprising B-10 can be o-carborane, m-carborane or p-carborane. More specifically, at least one molecule comprising B-10 is o-carborane. o-Carborane [1,2-dicarbadodecaborane(12)]; m-carborane [1,7-dicarbadodecaborane(12)]; and p-carborane [1,12-dicarbadodecaborane(12)] are commercially available from Aldrich, Milwaukee, Wis.

Specifically, each molecule comprising B-10 can independently be o-carborane, m-carborane or p-carborane. More specifically, each molecule comprising B-10 is o-carborane.

Compound of Formula I/Molecule Comprising B-10

The residue of molecule comprising B-10 can be linked to the residue of a compound of formula I through an amide (e.g., —N(R)C(=O)— or —C(=O)N(R)—), ester (e.g., —OC(=O)— or —C(=O)O—), ether (e.g., —O—), amino (e.g., —N(R)—), ketone (e.g., —C(=O)—), thioether (e.g., —S—), sulfinyl (e.g., —S(O)—), sulfonyl (e.g., —S(O)$_2$—), or a direct (e.g., C—C bond) linkage, wherein each R is independently H or (C$_1$–C$_6$)alkyl. Such a linkage can be formed from suitably functionalized starting materials using synthetic procedures that are known in the art. Based on the linkage that is desired, one skilled in the art can select suitably functional starting materials that can be derived from a residue of a compound of formula I and from a given residue of a molecule comprising B-10 using procedures that are known in the art.

The residue of the molecule comprising B-10 can be directly linked to any synthetically feasible position on the residue of a compound of formula I. Suitable points of attachment include, for example, the barboxamide, the d-carboxamide, and the e-carboxamide (illustrated in FIG. 1), as well as the 6position (the position occupied by X in FIG. 1), and the 5'-hydroxy and the 3'-hydroxy groups on the 5-membered sugar ring, although other points of attachment are possible. U.S. Pat. No. 5,739,313 discloses compounds (e.g., cyanocobalamin-b-(4-aminobutyl)amide, methylcobalamin-b-(4-aminobutyl)amide, and adenosylcobalamin-b-(4-aminobutyl)amide) that are useful intermediates for the preparation of compounds of the present invention.

Compounds wherein the residue of a molecule comprising B-10 is linked to the 6-position of a compound of formula I can be prepared by reducing a corresponding Co (II) compound of formula I to form a nucleophilic Co (I) compound and treating this Co (I) compound with a residue of a molecule comprising B-10 (or a derivative thereof) comprising a suitable leaving group, such as a halide (e.g., a chloride).

The invention also provides compounds having more than one residue of a molecule comprising B-10 directly linked to a compound of formula I. For example, the residue of a molecule comprising B-10 can be directly linked to a residue of the b-carboxamide of the compound of formula I and a residue of another molecule comprising B-10 can be directly linked to a residue of the d-carboxamide of the compound of formula I. In addition, the residue of a molecule comprising B-10 can be directly linked to the 6-position of the compound of formula I and a residue of another molecule comprising B-10 can be directly linked to a residue of the d- or e-carboxamide of the compound of formula I.

Compound of Formula I/Linker/Molecule Comprising B-10 Linker

In addition to being directly linked to the residue of a compound of formula I, the residue of a molecule comprising B-10 can also be linked to the residue of a compound of formula I by a suitable linker. The structure of the linker is not crucial, provided it yields a compound of the invention which has an effective therapeutic index against the target cells, and which will localize in or near tumor molecules.

Suitable linkers include linkers that separate the residue of a compound of formula I and the residue of a molecule comprising B-10 by about 5 angstroms to about 200 angstroms. Other suitable linkers include linkers that separate the residue of a compound of formula I and the residue of a molecule comprising B-10 by about 5 angstroms to about 100 angstroms, as well as linkers that separate the residue of a compound of formula I and the residue of a molecule comprising B-10 by about 5 angstroms to about 50 angstroms, or by about 5 angstroms to about 25 angstroms. Suitable linkers are disclosed, for example, in U.S. Pat. No. 5,735,313.

The linker can be linked to any synthetically feasible position on the residue of a compound of the residue of formula I. Suitable points of attachment include, for example, a residue of the b-carboxamide, a residue of the d-carboxamide, and a residue of the e-carboxamide, the 6-position (i.e., the position occupied by X in the compound of formula I), as well as a residue of the 5'-hydroxy group and a residue of the 3'-hydroxy group on the 5-membered sugar ring, although other points of attachment are possible. Based on the linkage that is desired, one skilled in the art can select suitably functionalized starting materials that can be derived from a compound of formula I and from a given molecule comprising B-10 using procedures that are known in the art.

The linker can conveniently be linked to the residue of a compound of formula I or to the residue of a molecule comprising B-10 through an amide (e.g., —N(R)C(=O)— or —C(=O)N(R)—), ester (e.g., —OC(=O)— or —C(=O)O—), ether (e.g., —O—), ketone (e.g., —C(=O)—) thioether (e.g., —S—), sulfinyl (e.g., —S(O)—), sulfonyl (e.g., —S(O)$_2$—), amino (e.g., —N(R)—) or a direct (e.g., C—C) linkage, wherein each R is independently H or (C$_1$–C$_6$)alkyl. The linkage can be formed from suitably functionalized starting materials using synthetic procedures that are known in the art. Based on the linkage that is desired, one skilled in the art can select suitably functional starting materials that can be derived from a residue of a compound of formula I, a residue of a molecule comprising B-10, and from a given linker using procedures that are known in the art Specifically, the linker can be a divalent radical of the formula W—A—Q wherein A is (C$_1$–C$_6$)alkyl, (C$_2$–C$_6$) alkenyl, (C$_2$–C$_6$)alkynyl, (C$_3$–C$_8$)cycloalkyl, or (C$_6$–C$_{10}$) aryl, wherein W and Q are each independently —N(R)C (=O)—, —C(=O)N(R)—, —OC(=O)—, —C(=O)—, —O—, —S—, —S(O)—, —S(O)₂—, —N(R)—, —C(=O)—, or a direct bond (i.e., W or Q is absent); wherein each R is independently H or (C₁-C₆)alkyl.

Specifically, the linker can be a divalent radical of the formula W—(CH₂)ₙ—Q wherein, n is between about 1 and about 20, between about 1 and about 15, between about 2 and about 10, between about 2 and about 6, or between about 4 and about 6; wherein and Q are each in dependently —N(R)C(=O)—, —C(=O)N(R)—, —OC(=O)—, —C(=O)O—, —O—, —S—, —S(O)—, —S(O)₂—, —C(=O)—, —N(R)—, or a direct bond (i.e., W or Q is absent); wherein each R is independently H or (C₁-C₆)alkyl.

Specifically, W and Q are each independently —N(R)C(=O)—, —C(=O)N(R)—, —OC(=O)—, —N(R)—, —C(=O)O—, —O—, or a direct bond (i.e., W or Q is absent).

Specifically, the linker is a divalent radical, i.e., 1,ω-divalent radicals formed from a peptide or an amino acid. The peptide can comprise 2 to about 20 amino acids, 2 to about 15 amino acids, or 2 to about 12 amino acids.

Specifically, the peptide can be poly-L-lysine (i.e., [—NHCH[(CH₂)₄NH₂]CO—]ₘ—Q, wherein Q is H, (C₁-C₁₄)alkyl, or a suitable carboxy protecting group; and wherein m is about 2 to about 20. Specifically, the poly-L-lysine can contains about 5 to about 15 residues (i.e., m is between about 5 and about 15). More specifically, the poly-L-lysine can contain about 8 to about 11 residues (i.e., m is between about 8 and about 11).

Specifically, the peptide can be poly-L-glutamic acid, poly-L-aspartic acid, poly-L-histidine, poly-L-ornithine, poly-L-serine, poly-L-threonine, poly-L-tyrosine, poly-L-lysine-L-phenylalanine or poly-L-lysine-L-tyrosine.

Specifically, the linker is prepared from 1,6-diaminohexane H₂N(CH₂)₆NH₂, 1,5-diaminopentane H₂N(CH₂)₅NH₂, 1,4diaminobutane H₂N(CH₂)₄NH₂., or 1,3-diaminopropane H₂N(CH₂)₃NH₂.

The linker can comprise one or more non-metallic radionuclides. Specifically, the linker can comprise more than one non-metallic radionuclides. More specifically, the linker can comprise 2 to about 10, 2 to about 8, 2 to about 6, or 2 to about 4 non-metallic radioisotopes.

A specific residue of a peptide (i.e., linker) comprising one or more non-metallic radionuclides has the following formula

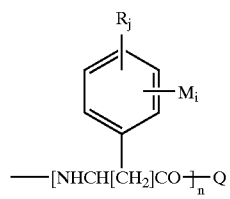

wherein each M is independently a non-metallic radionuclide; each R is independently (C₂-C₁₄)alkyl, (C₂-C₁₄)alkenyl, (C₂-C₁₄)alkynyl, (C₁-C₁₄)alkoxy, hydroxy, cyano, nitro, halo, trifluoromethyl, N(Rₐ)(Rᵦ), (C₁-C₁₄)alkanoyl, (C₂-C₁₄)alkanoyloxy, (C₆-C₁₀)aryl, or (C₃-C₈)cycloalkyl wherein Rₐ and Rᵦ are each independently H or (C₁-C₁₄)alkyl; P; Q is H, (C₁-C₁₄)alkyl, or a suitable carboxy protecting group; n is 2 to about 20; I is 1–5, j is 0–4 and I+j is ≦5; or a pharmaceutically acceptable salt thereof.

Specifically, i can be 1, j can be 0, M can be Fluorine-18, Bromine-76, or Iodine-123, and n can be about 6 to about 12.

The molecule comprising B-10 can comprise one or more boron atoms. A suitable molecule comprising B-10 can contain 1 to about 20, 1 to about 15, 1 to about 10, or 1 to about 5 boron atoms. In addition, the molecule comprising B-10 can comprise one or more B-10 atoms. A suitable molecule comprising B-10 can contain 1 to about 20, 1 to about 15, 1 to about 10, or 1 to about 5 B-10 atoms.

The molecule comprising B-10 can be an amino acid, a carbohydrate, a nucleoside or a carborane. Specifically, the molecule comprising B-10 is o-carborane, m-carborane or p-carborane.

Compounds wherein the linker is linked to the 6position of a compound of formula I can be prepared by preparing a nucleophilic Co (I) species as described herein above, and reacting it with a linker comprising a suitable leaving group, such as a halide (e.g. a chloride).

The invention also provides compounds having more than one molecule comprising B-10 attached to a compound of formula I, each through a linker. For example, the residue of a molecule comprising B-10 can conveniently be linked, through a linker, to a residue of the b-carboxamide of the compound of formula I and a residue of another molecule comprising B-10 can conveniently be linked, through a linker, to a residue of the d- or e-carboxamide of the compound of formula I. In addition, the residue of a molecule comprising B-10 can conveniently be linked, through a linker, to the 6-position of the compound of formula I and a residue of another molecule comprising B-10 can conveniently be linked, through a linker, to a residue of the b-, d- or e-carboxamide of the compound of formula I.

The invention also provides compounds having more than one molecule comprising B-10 attached toga compound of formula I, either directly or through a linker. For example, the residue of a molecule comprising B-10 can conveniently be linked, either directly or through a linker, to a residue of the b-carboxamide of the compound of formula I and a residue of another molecule comprising B-10 can conveniently be linked, either directly or through a linker, to a residue of the d- or e-carboxamide of the compound of formula I. In addition, the residue of a molecule comprising B-10 can conveniently be linked, either directly or through a linker, to the 6position of the compound of formula I and a residue of another molecule comprising B-10 can conveniently be linked, either directly or through a linker, to a residue of the b-, d- or e-carboxamide of the compound of formula I.

Compound of Formula I/Chelating Group Comprising Gadolinium-157

U.S. Pat. No. 5,739,313 discloses cobalamin analogs comprising a compound of formula I, a linking group, and a chelating group comprising a detectable radionuclide or a paramagnetic ion. The compounds are disclosed to localize in tumor cells following administration, and to be useful for imaging tumors.

The metallic radionuclide Gadolinium-157 is an especially useful ion for conducting magnetic resonance imaging. It is also a useful target ion for neutron capture therapy. Applicants have discovered that incorporation of Gd-157 into one of the chelating molecules disclosed in U.S. Pat. No. 5,739,313, provides a compound that is not only particularly useful for conducting magnetic resonance imaging, but also a compound that can be used in conjunction with neutron capture therapy, to treat tumors.

Thus, the present invention provides a residue of a compound of formula I linked to at least one residue of the formula —Q—L—W—Det; wherein each Det is independently a chelating group comprising Gd-157; each L is independently linker (as defined hereinabove) or is absent;

and each W and Q are each independently —N(R)C(=O)—, —C(=O)N(R)—, —OC(=O)—, —C(=O)O—, —O—, —S—, —S(O)—, —S(O)—, —C(=O), —N(R)—, or a direct bond (i.e., W or Q is absent); wherein each R is independently H or ($C_1$–$C_6$)alkyl.

Compound of Formula I/Chelating Group Comprising a Radionuclide

Applicant has also discovered that it is possible to prepare a compound that is useful for both imaging and for treating tumors by incorporating one or more neutron capture target atoms (e.g. B-10 or Gd-157) into a compound that also comprises a detectable radionuclide. Accordingly, the invention provides a residue of a compound of formula I which is linked to one or more residues of a molecule comprising B-10; and which is also linked to one or more groups of the formula —Q—L—W—Det; wherein each Det is independently a chelating group (as defined herein) comprising Gd-157; each L is independently linker (as defined herein) or is absent; and each W and Q are each independently —N(R)C(=O)—, —C(=O)N(R)—, —OC(=O)—, —C(=O)O—, —O—, —S—, —S(O)—, —S(O)$_2$—, —C(=O)—, —N(R)—, or a direct bond (i.e., W or Q is absent); wherein each R is independently H or ($C_1$–$C_6$)alkyl; or a pharmaceutically acceptable salt thereof.

The present invention provides a residue of a compound of formula I linked to a molecule comprising B-10 or linked to a chelating group comprising Gd-157 and wherein the residue of a compound of formula I is linked to at least one residue of the formula —Q—W—Det; wherein each Det is independently a chelating group (as defined hereinabove) comprising a metallic radionuclide; each L is independently a linker (as defined hereinabove) or is absent; and each W and Q are each independently —N(R)C(=O)—, —C(=O)N(R)—, —OC(=O)—, —C(—O)O—, —O—, —S—, —S(O)—, —S(O)$_2$—, —C(=O)—, —N(R)—, or a direct bond (i.e., W or Q is absent); wherein each R is independently H or ($C_1$–$C_6$)alkyl.

Compound of Formula I/Molecule Comprising B-10/Detectable Radionuclide

The invention also provides a compound wherein a residue of a compound of formula I (FIG. 1) is linked 1) to a residue of a molecule comprising B-10, and 2) to a detectable radionuclide, wherein X is CN, OH, $CH_3$, adenosyl, or a molecule comprising B-10; or a pharmaceutically acceptable salt thereof The detectable radionuclide can be directly linked to the residue of a compound of formula I, or can be linked by a linker to the residue of a compound of formula I. The linker can be any suitable linker described herein Specifically, the linker can be of the formula W—A wherein A is ($C_1$–$C_6$) alkyl, ($C_2$–$C_6$)alkenyl, ($C_2$–$C_6$)alkynyl, ($C_3$–$C_8$)cycloalkyl, or ($C_6$–$C_{10}$)-aryl, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or ($C_1$–$C_6$) alkyl; and wherein A is substituted with one or more non-metallic radionuclides. The linker can also be a peptide or an amino acid.

Compound of Formula I/Group comprising Gd-157/Detectable Radionuclide

The invention also provides a compound wherein a residue of a compound of formula I (FIG. 1) is linked 1) to a detectable radionuclide; and 2) to a group comprising Gd-157; or a pharmaceutically acceptable salt thereof The Gd-157 can be linked to the residue of a compound of formula I by any suitable means. For example, the residue of a compound of formula I can be attached to a group comprising Gd-157 that has the formula Q—L—W—Det, wherein Det is a chelating group comprising Gd-157, L is a linker or absent, and W and Q are each independently —N(R)C(=O), —C(=O)N(R)—, —OC(=O)—, —C(=O)O—, —O—, —S—, —S(O)—, —S(O)$_2$—, —C(=O)—, —N(R)—, or a direct bond; wherein each R is independently H or ($C_1$–$C_6$)alkyl. Any suitable chelator can be used.

The detectable radionuclide can be directly linked to the residue of a compound of formula I, or can be linked by a linker to the residue of a compound of formula I. The linker can be any suitable linker described herein. Specifically, the linker can be is of the formula W—A wherein A is ($C_1$–$C_6$) alkyl, ($C_2$–$C_6$)alkenyl, ($C_2$–$C_6$)alkynyl, ($C_3$–$C_8$)cycloalkyl, or ($C_6$–$C_{10}$)aryl, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or ($C_1$–$C_6$)-alkyl; and wherein A is substituted with one or more non-metallic radionuclides. The linker can also be a peptide or an amino acid

Non-metallic Radionuclide

Any detectable non-metallic radionuclide that is suitable for imaging can be used in the compounds of the invention. For example, suitable non-metallic radionuclides include Carbon-11, Fluorine-18, Bromine-76, and Iodine-123. Specifically, the non-metallic radionuclide can be a non-metallic paramagnetic atom (e.g., Fluorine-19); or a non-metallic positron emitting radionuclide (e.g., Carbon-11, Fluorine-18, Iodine-123, or Bromine-76).

Metallic Radionuclide

Suitable metallic radionuclides (i.e., metallic radioisotopes or metallic paramagnetic ions) include Antimony-124, Antimony-125, Arsenic-74, Barium-103, Barium-140, Beryllium-7, Bismuth-206, Bismuth-207, Cadmium-109, Cadmium-115 m, Calcium45, Cerium-139, Cerium-141, Cerium-144, Cesium-137, Chromium-51, Cobalt-55, Cobalt-56, Cobalt-57, Cobalt-58, Cobalt-60, Cobalt64, Copper-67, Erbium-169, Europium-152, Gallium-64, Gallium-68, Gadolinium-153, Gadolinium-157 Gold-195, Gold-1 99, Hafnium-175, Hafnium-175–181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+ 191, Palladium-103, Platinum-195 m, Praseodymium-143, Promethium-147, Protactinium-233, Radium-226, Rhenium-1 86, Rhenium-1 88, Rubidium-86, Ruthenium-103, Ruthenium-106, Scandium44, Scandium-46, Selenium-75, Silver-110 m, Silver-111, Sodium-22, Strontium-85, Strontium-89, Strontium-90, Sulfur-35, Tantalum-182, Technetium-99 m, Tellurium-125, Tellurium-132, Thallium-204, Thorium-228, Thorium-232, Thallium-170, Tin-113, Tin-114, Tin-117 m Titanium44, Tungsten-1 85, Vanadium48, Vanadium49, Ytterbium-169, Yttrium-86, Yttrium-88, Yttrium-90, Yttrium-91, Zinc65, and Zirconium-95.

As used herein, a "detectable radionuclide" is any suitable radionuclide (i.e., radioisotope) capable of detecting cancer or other neoplastic cells in a diagnostic procedure in vivo or in vitro. Suitable detectable radionuclides include metallic radionuclides (i.e., metallic radioisotopes) and non-metallic radionuclides (i.e., non-metallic radioisotopes).

As used herein, a "therapeutic radionuclide" is any suitable radionuclide (i.e., radioisotope) that possesses therapeutic efficacy against cancer or other neoplastic cells in vivo or in vitro. Suitable therapeutic radionuclides include metallic radionuclides (i.e., metallic radioisotopes).

Chelating Groups

Any suitable chelating group can be incorporated into the compounds of the invention. Suitable chelating groups include those disclosed in U.S. Pat. No. 5,739,313. Specifically, the chelating group can be NTA, HEDTA, DCTA, RP414, MDP, DOTATOC, CDTA, HYNIC, EDTA, DTPA, TETA, DOTA, DOTMP, DCTA, 15N4, 9N3, 12N3, or MAG3 (or another suitable polyamino acid chelator),. which are described herein below, or a phosphonate chelator (e.g. EDMT). More specifically, the chelating group can be DTPA.

DTPA is diethylenetriaminepentaacetic acid; TETA is 1,4,8,11-tetraazacyclotetra-decane-N,N',N'',N'''-tetraacetic acid; DOTA is 1,4,7,10-tetraazacyclododecane-N,N',N'',N'''-tetraacetic acid; 15N4 is 1,4,8,12-tetraazacyclopentadecane-N,N',N'',N'''-tetraacetic acid; 9N3 is 1,4,7-triazacyclononane-N,N',N''-triacetic acid; 12N3 is 1,5,9-triazacyclododecane-N,N',N''-triacetic acid; MAG3 is (N-[N-[N-[(benzoylthio)acetyl]-glycyl]glycyl]glycine); and DCTA is a cyclohexane-based metal chelator of the formula

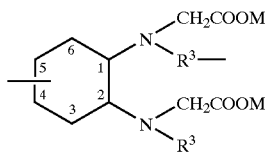

wherein $R^3$ may by $(C_1-C_4)$alkyl or $CH_2CO_2$—, which may be attached through positions 4 or 5, or through the group $R^3$ and which carries from 1 to 4 detectable metal or nonmetal cations (M), monovalent cations, or the, alkaline earth metals. Thus, with metals of oxidation state +1, each individual cyclohexane-based molecule may carry up to 4 metal cations (where both $R^3$ groups are $CH_2COOM$). As is more likely, with higher oxidation states, the number of metals will decrease to 2 or even 1 per cyclohexane skeleton. This formula is not intended to limit the molecule to any specific stereochemistry.

NTA, HEDTA, and DCTA are disclosed in Poster Sessions, Proceedings of the 46th Annual Meeting, *J. Nuc. Med.*, p. 316, No. 1386. RP414 is disclosed in Scientific Papers, Proceedings of the 46th Annual Meeting, *J. Nuc. Med.*, p. 123, No. 499. MDP is disclosed in Scientific Papers, Proceedings of the 46th Annual Meeting, *J. Nuc. Med.*, p. 102, No. 413. DOTATOC is disclosed in Scientific Papers, Proceedings of the 46th Annual Meeting, *J. Nuc. Med.*, p. 102, No. 414 and Scientific Papers, Proceedings of the 46th Annual Meeting, *J. Nuc. Med.*, p. 103, No. 415. CDTA is disclosed in Poster Sessions, Proceedings of the 46th Annual Meeting, *J. Nuc. Med.*, p. 318, No. 1396. HYNIC is disclosed in Poster Sessions, Proceedings of the 46th Annual Meeting, *J. Nuc. Med.*, p. 319, No. 1398.

Bifunctional chelators (i.e., chelating groups) based on macrocyclic ligands in which conjugation is via an activated arm attached to the carbon backbone of the ligand can also be employed as a chelating group, as described by M. Moi et al., J. Amer. Chem., Soc., 49, 2639 (1989) (2-p-nitrobenzyl-1,4,7,10-tetraazacyclododecane-N,N',N'',N'''-tetraacetic acid); S. V. Deshpande et al., J. Nucl. Med., 31, 473 (1990); G. Kuser et al., Bioconj. Chem., 1, 345 (1990); C. J. Broan et al., J. C. S. Chem. Comm., 23, 1739 (1990); and C. J. Anderson et al., J. Nucl. Med. 36, 850 (1995) (6-bromoacetamido-benzyl-1,4,8,11-tetraazacyclotetadecane-N,N',N'',N'''-tetraacetic acid (BAT)).

In addition, the diagnostic chelator or therapeutic chelating groups can be any of the chelating groups disclosed in Scientific Papers, Proceedings of the 46th Annual Meeting, *J. Nuc. Med.*, Wednesday, Jun. 9, 1999, p. 124, No. 500.

A "detectable chelating group" is a chelating group comprising a metallic radionuclide (e.g., a metallic radioisotope) capable of detecting cancer or other neoplastic cells in vivo or in vitro.

Specifically, the chelating group can be any one of the carbonyl complexes disclosed in Waibel et al., *Nature Biotechnology*, 897–901, Vol. 17, September 1999; or Sattelberger et al., *Nature Biotechnology*, 849–850, Vol. 17, September 1999.

Specifically, the detectable chelating group can be any of the carbonyl complexes disclosed in Waibel et al., *Nature Biotechnology*, 897–901, Vol. 17, September 1999; or Sattelberger et al., *Nature Biotechnology*, 849–850, Vol. 17, September 1999, further comprising a metallic radionuclide. More specifically, the detectable chelating group can be any of the carbonyl complexes disclosed in Waibel et al., *Nature Biotechnology*, 897–901, Vol. 17, September 1999; or Sattelberger et al., *Nature Biotechnology*, 849–850, Vol. 17, September 1999, further comprising Technetium-99 m.

As used herein, a "therapeutic chelating group" is a chelating group comprising a metallic radionuclide (e.g., a metallic radioisotope) that possesse therapeutic efficacy against cancer or other neoplastic cells in vivo or in vitro. Any suitable chelating group can be employed.

Specifically, the therapeutic chelating group can be any of the carbonyl complexes disclosed in Waibel et al., *Nature Biotechnology*, 897–901, Vol. 17, September 1999; or Sattelberger et al., *Nature Biotechnology*, 849–850, Vol. 17, September 1999, further comprising a metallic radionuclide. More specifically, the therapeutic chelating group can be any of the carbonyl complexes disclosed in Waibel et al., *Nature Biotechnology*, 897–901, Vol. 17, September 1999; or Sattelberger et al., *Nature Biotechnology*, 849–850, Vol. 17, September 1999, further comprising Rhenium-186 or Rhenium-188.

Tumors treatable with the compounds and methods of the invention can be located in any part of the mammal. Specifically, the tumor can be located in the breast, lung, thyroid, lymph node, genitourinary system (e.g., kidney, ureter, bladder, ovary, teste, or prostate), musculoskeletal system (e.g., bones, skeletal muscle, or bone marrow), gastrointestinal tract (e.g., stomach, esophagus, small bowel, colon, rectum, pancreas, liver, or smooth muscle), central or peripheral nervous system (e.g., brain, spinal cord, or nerves), head and neck tumors (e.g., ears, eyes, nasopharynx, oropharynx, or salivary glands), or the heart.

The compounds disclosed herein can be prepared using procedures similar to those described in U.S. Pat. No. 5,739,313, or using procedures similar to those described herein. The residue of a molecule comprising B-10 can be linked to the residue of a compound of formula I as described hereinabove. Additional intermediates and synthetic procedures useful for preparing compounds of the invention are disclosed, for example, in Hogenkamp, H. et al., *Synthesis and Characterization of nido-Carborane-*

*Cobalamin Conjugates*, Nucl. Med. & Biol., 2000, 27, 89–92; Collins, D., et al., *Tumor Imaging Via Indium* 111-*Labeled DTPA-Adenosylcobalamin*, Mayo Clinic Proc., 1999, 74:687–691; U.S. application Ser. No. 60/129,733 filed Apr. 16, 1999; U.S. application Ser. No. 60/159,874 filed Oct. 15, 1999; U.S. application Ser. No. 60/159,753 filed Oct. 15, 1999; U.S. Application Ser. No. 60/159,873 filed Oct. 15, 1999; and references cited therein.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as pharmaceutical compositions and administered to a mammalian host, such as a human patient in a variety of forms adapted to the chosen route of administration, i.e., orally or parenterally (e.g., by intravenous, intramuscular, intraperitoneal). Preferably, the compounds are administered parenterally.

The active compound may also be administered intravenously or intraperitoneally by infuision or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For illustration, suitable doses of a compound of the invention for use in therapy, in conjunction with neutron capture, include doses in the range of from about 0.1 μg to about 100 μg, e.g., from about 0.5 μg to about 50 μg, or from about 0.5 μg to 15 μg per treatment. Suitable doses for use in imaging or for use in imaging and therapy include doses in the range of from about 0.1 mg to about 50 g, e.g., from about 0.5 mg to about 10 g, or from about 0.5 g to 2 g per treatment.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds are preferably dissolved or dispersed in a nontoxic liquid vehicle, such as physiological saline or a similar aqueous vehicle, to the desired concentration. A preselected therapeutic unit dose is then administered to the test animal or human patient, by oral administration or ingestion or by parenteral administration, as by intravenous or intraperitoneal infusion or injection, to attain the desired in vivo concentration. Doses useful for treating tumors can be derived, from those found to be effective to treat tumors in humans in vitro or in animal models, such as those described hereinbelow, or from dosages of other labeled vitamin $B_{12}$ molecules, previously employed in animal therapy.

Figure 2:
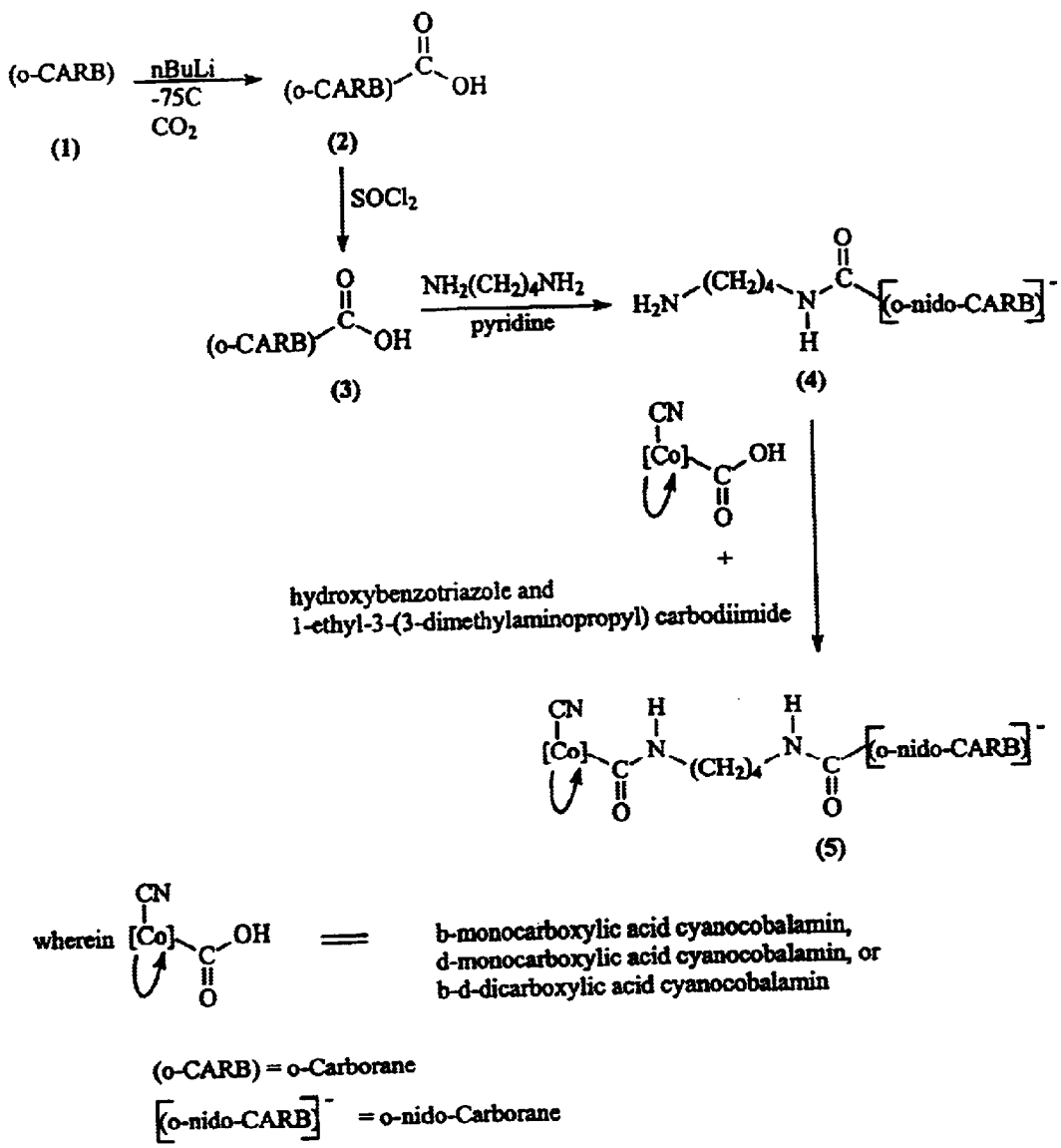
FIG. 2 illustrates the synthesis of a cyanocobalamin-nido-carborane conjugate.
Figure 3:
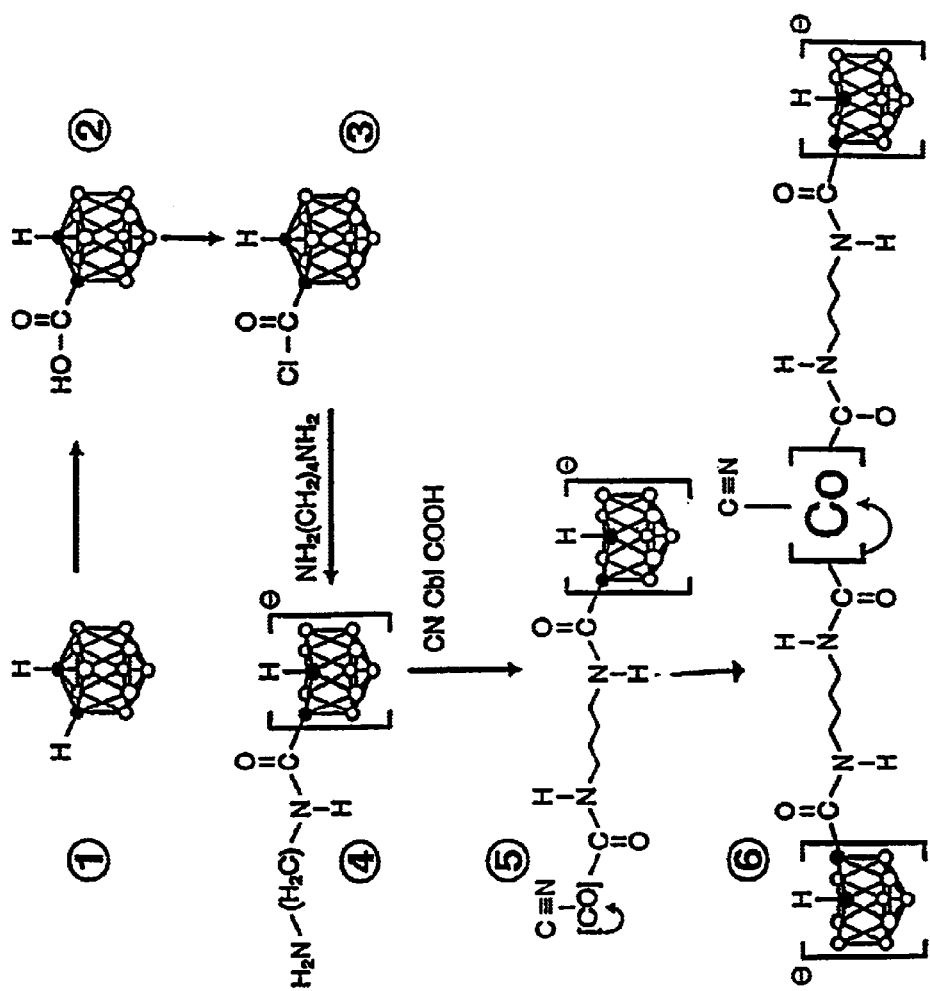
FIG. 3 illustrates the synthesis of representative compounds of the present invention.

FIG. 2 and FIG. 3 each illustrate the four step synthesis used to prepare three cyanocobalamin-nido-carborane conjugates, o-Carborane carboxylic acid (2) was prepared by reacting o-carborane with n-butyllithium and carbon dioxide in ether for approximately one hour at −78° C. Treatment with thionyl chloride gave o-carborane carboxylic acid chloride (3), which was allowed to react with 1,4-butanediamine in pyridine to give the amide linked nido-carboranoyl(4aminobutyl)amide (4). Compound (4) was linked to the b-monocarboxylic acid of cyanocobalamin, the d-monocarboxylic acid of cyanocobalamin, or both the b- and d-dicarboxylic acid of cyanocobalamin. In each reaction, hydroxybenzotriazole and 1-ethyl-3-(3-dimethylaminopropyl) carbodiimide was added to facilitate the formation of the amide bond.

The invention may be further illustrated by the following examples.

EXAMPLES

Ultraviolet-visible spectra were recorded with a diode array spectrophotometer. $^{11}$B NMR spectra at 192.656 MHZ with $^{1}$H decoupling were recorded on Varian 1NOVA 600 MHZ spectrometer with an 8 mm broad band probe. Approximately 10 mg of the cobalamin-conjugate were dissolved in 1 mL pyridine $d_6$ in a 5 mm NMR tube. Five hundred scans were collected with an acquisition time of 0.133 seconds and a relaxation delay of 1 second. Chemical shifts are given relative to $BF_3$:$(CH_3CH_2)_2O$.

Mass spectral data was obtained on a Sciex API 365 LC-MS/MS system (Toronto, Canada). Separations were done on a Shimadzu HPLC system consisting of two LC-10AD pumps and a SCL-10Avp controller (Shimadzu Scientific Instruments, Columbia, Md.). Analytes were monitored by UV at 214 NM with an ABI 785 detector. HPLC separations were achieved using a BDS-Hypersil C8 column (150×4.6 mm; 120 A, Keystone Scientific, Inc., Bellefonte, Pa.). The mobile phase consisted of $H_2O$: methanol (98:2 v:v) in pump A and $H_2O$: methanol (2:92 v:v) in pump B. A linear gradient was used from 5% B to 30% B over 10 minutes and was held at 30% B for 20 minutes before returning to initial conditions (mono-carborane synthesis). The di-carborane required a longer gradient using the same mobile phases; 5% B to 65% B over 25 minutes and held at 65% B for 15 minutes before returning to initial conditions. The separations were monitored by UV absorption at 214 NM. The flow was 1.0 ml/minute and was split post-column allowing ~10 µL to flow into the mass spectrometer.

Mass spectral data was collected using electrospray ionization in positive mode over a mass range of 300 to 2300 AMU at a dwell time of 0.3 ms/0.1 AMU. Synthetic samples were prepared at 5 or 10 mg/ml in pump A mobile phase and an aliquot injected onto the HPLC (1–5 µL). Retention times of the mono-and di-carborane products were determined to be 13.3 minutes and 16.2 minutes respectively. Purification of the b and d mono-carborane products was achieved by collecting fractions at the elution times for several injections. The collected fractions were combined and dried to a powder. A portion of the purified product was dissolved in methanol:$H_2O$ (1:1) and reanalyzed by BPLC-MS to ascertain the purity.

o-Carborane, butyllithium (1.6 M solution in hexanes) and putrescine were purchased from Aldrich Chemical Company (Milwaukee, Wis.). The water-soluble carbodiimide 1-ethyl-3(3'-dimethylaminopropyl) carbodiimide and 1-hydroxybenzotriazole were from Sigma (St. Louis, Mo.). Thin layer chromatography (TLC) silica gel plates were obtained from Eastman Kodak Company. The cyanocobalamin-b, d, and e monocarboxylic acids and the b, d-dicarboxylic acid were prepared as described before (see U.S. Pat. No. 5,739,313, and D. L. Anton, et al., *J. Am. Chem. Soc.*, 1980, 102, 2212–2219), and were provided by Professor Kahl of the Department of Medicinal Chemistry at the University of California, San Francisco.

Example 1

Cyanocobalamin-nido-carborane conjugates (5, FIG. 2). Separate reaction mixtures containing 1 g (~0.66 nimol) of the b-monocarboxylic acid, d-monocarboxylic acid, or the b,d-dicarboxylic acid of cyanocobalamin, hydroxybenzotriazole (810 mg, 6.0 mmol), 1-ethyl-3(3-dimethylaminopropyl) carbodiimide (11.4 g, 6.0 mmol) and 4 (600 mg, 2.0 mmol) in 100 mL of a water-acetone mixture (2:1) were adjusted to pH 6.9 with 1N NaOH. The reactions were stirred at room temperature and their progress monitored by TLC. After 3 hours, the mixtures were concentrated to remove acetone and the resulting aqueous suspensions were extracted into 92% aqueous phenol. The phenol phases were washed with water to remove the water-soluble reactants. One volume of acetone and three volumes of ether were added to each of the phenol phases and the desired cyanocobalamin-nido-carborane conjugates were back extracted into water. The aqueous layers were extracted three times with ether to remove residual phenol and unreacted (4). Finally the aqueous solutions were evaporated to dryness. The residuals were triturated with acetone and the desired conjugates isolated as orange-red powders (yields 90–95% based on the cyanocobalamin-carboxylic acids).

The isotope ratios of the final products were also compared to theoretical as follows: Mono product theoretical M+H$^+$ ($C_{70}H_{109}CoB_9O_{15}PN_{15}$)—1584.8 (12%), 1585.8 (37%), 1586.8 (74%), 1587.8 (100%), 1588.8 (84%), 1589.8 (44%), 1590.8 (16%), 1591.8 (4%). Synthesis I—1584.8 (14%), 1585.8 (37%), 1586.8 (74%), 1587.8 (100%), 1588.8 (88%), 1589.8 (48%), 1590.8 (19%), 1591.8 (6%). Synthesis H—1584.8 (15%), 1585.8 (40%), 1586.8 (78%), 1587.8 (1000), 1588.8 (86%), 1589.8 (44%), 1590.8 (17%), 1591.8 (7%).

Di product theoretical M+H$^+$—($C_{77}H_{129}CoB_{18}O_{16}PN_{16}$)—1815.1 (9%), 1816.1 (23%), 1817.1 (47%), 1818.1 (77%), 1819.1 (99%), 1820.1 (100%), 1821.1 (77%), 1822.1 (44%), 1823.1 (19%), 1824.1 (6%). Observed synthesis—1815.1 (15%), 1816.1 (27%), 1817.1 (51%), 1818.1 (79%), 1819.1 (100%), 1820.1 (100%), 1821.1 (78%), 1822.1 (49%), 1823.1 (25%), 1824.1 (12%).

Results included the identification of the b and d carborane cyanocobalamin (CCC) analogs by LC-MS. Products identified were subsequently separated and purified by HPLC. The purified products were reanalyzed by LC-MS with no starting material detected. MS/MS data was also obtained on the b and d CCC analogs to provide further structural characterization. These purified products were then tested in the biological assays. The e-CCC analog and the di-CCC analog were also separated and identified by LC-MS, however, the preparations contained more reaction side products resulting in difficult purification. The isotope ratios of the b- and d-CCC analogs, as well as the di-CCC analog, were compared to theoretical isotope ratios to provide further information for identification.

Mass spectra confirmed the presence of each cyanocobalamin-nido-carborane conjugate. Mass spectroscopy analysis as well as $^{11}$B NMR showed that during the conversion of 3 to 4 (FIGS. 2 and 3) the o-carborane nucleus lost a boron atom to yield the nido-carborane derivative 4 (FIG. 3). UV-visible spectroscopy of the final products showed maxima typical of cyanocobalamin, indicating that the corrin nucleus was intact and that the 5,6-dimethyl benzimadazole nucleotide was still attached to the cobalt atom.

The starting material 4 was prepared as follows (see FIG. 2):

a o-Carborane carboxylic acid (2). A solution of o-carborane (1) (5.0 g, 34.7 mmol) in 500 ml dry ether in a 1 L round bottom flask was cooled to −78° C. in a dry ice-acetone bath The solution was flushed with argon and the flask sealed with a serum stopper. n-Butyllithium (24 mL, 1.6 M in hexanes) was slowly injected via a syringe over a period of about 20 minutes and the reaction was stirred for an additional 30 minutes. Crushed dry ice (10–15 g) was then added and the mixture stirred for 1 hour. The dry ice-acetone bath was removed and the reaction allowed to come to room temperature. The ether and hexanes were removed on a rotary evaporator, water (150 ml) was added and unreacted o-carborane was id removed by extraction with hexanes (2×100 ml). The aqueous phase was acidified with tn concentrated HCl and the desired product extracted with hexanes (4×100 ml). The combined extracts were dried over $Na_2SO_4$ and evaporated to dryness to give 5.8 g (88.7%) of o-Carborane carboxylic acid (2), which was used without further purification.

b. o-Carborane carboxylic acid chloride (3), o-Carborane carboxylic acid (2.0 g, 10.6 mmol), dried over $P_2O_5$, was dissolved in 30 ml thionylchloride and heated under reflux for 3 hours. The solution was cooled to room temperature, evaporated to dryness and dried over P$_2$O$_5$ (2.05 g, 9.9 mmol, 93%) to provide (3), which was used without further purification.

c. Nido-Carboranoyl(4aminobutyl)amide (4). The acid chloride (3) was dissolved in 15 ml dry pyridine and 1,4-diaminobutane (1.12 g, 12.7 mmol) was added. The reaction mixture was heated under reflux for 3 hours, cooled to room temperature and concentrated. Water (10 ml) was added and the suspension acidified with 3 M HCl. The desired product was extracted with ethyl acetate (4×50 ml), the combined organic layers were washed once with-water, dried over Na$_2$SO$_4$ and evaporated to dryness to yield 2.35 g (8.0 mmol, 75%) of (4). Thus far the product has resisted crystallization from a variety of solvent mixtures, however TLC on silica gel plates (2-propanol-NH$_4$OH—H$_2$O; 7:1.2) showed only one ninhydrin positive compound distinct from the diamine.

Example 2

6-Carboranoylamidopropyl cobalamin. 6-(3-aminoprop-1-yl)cobalamin (300 mg), hydroxybenzotriazole (270 mg), 1-ethyl-3-(3-dimethylaminopropyl)carbodiimide (382 mg) and o-carborane monocarboxylic acid were dissolved in water (50 ml) and acetone (20 ml) and allowed to react at room temperature for 3 hours. The reaction mixture was concentrated to remove acetone and desalted via phenol extraction. The concentrated aqueous solution was crystallized from aqueous acetone to give the title compound.

The intermediate 6-(3-aminoprop-1-yl)cobalamin was prepared as follows: Cyano cobalamin (500 mg) was dissolved in 100 ml deoxygenated water containing 10 mg CoCl$_2$, and reduced with sodium borohydride to give the corresponding Co (I) compound. After 30 minutes, 3-chloropropyl amine hydrochloride (130 mg) dissolved in 5 ml deoxygenated ethanol was added. After one hour, at room temperature, the mixture was desalted via phenol extraction The aminopropylcarbolamine was back extracted into water after the addition of 1 volume of acetone and 3 volumes of ether. The aqueous solution was concentrated and the desired 6-(3-aminoprop-1-yl)cobalamin crystallized from aqueous acetone (yield 510 mg).

Example 3

DTPA-aminopropylcarbalamin (DAPC). Using a coupling procedure similar to that described in Example 2, 6-(3-aminoprop-1-yl)-cobalamin and DTPA were coupled in the presence of hydroxybenzotriazole to give the title compound.

Example 4

In vitro biological activity of the carborane cyanocobalamin analogs. To assess the in vitro binding of the carborane cyanocobalamin (Example 1, CCC) and DTPA-aminopropylcobalamin (Example 3, DAPC) analogs to the transcobalamin proteins, the unsaturated Vitamin B12 binding capacity (UBBC) assay (see D. A. Collins and H. P. C. Hogenkamp, *J. Nuclear Medicine*, 1997, 38, 717–723) was performed. Serum was obtained from 5 patients being evaluated for pernicious anemia at the Mayo Clinic. The patients' serum first underwent a routine clinical UBBC as previously described. To determine if the CCC and DAPC analogs would inhibit Co-57 cyanocobalamin from binding to the transcobalamin proteins, the excess serum from the 5 patients underwent modified UBBC.

Specifically, under dim light, 0.4 ml serum was treated with 4 μL (concentration 10 μg CCC per ml normal saline) of the 2 CCC analogs, carborane-d-cyano-cobalamin and carborane-b-cyanocobalamin, and DAPC. The analogs were incubated for 20 minutes at room temperature with the patient's serum. Both the clinical run and the analog treated samples were assayed for UBBC as usual.

The analogs competitively blocked Co-57-cyanocobalamin from binding to the transcobalamin proteins. Therefore, the cpm of the modified UBBC assay was significantly lower than that of the clinical runs. The percent PB of the analogs to transcobalamin protein was calculated as follows (PB=100−CCC$_{UBBC}$ cpm/clinical UBBC cpm× 100). The average percent binding (PB) of the 5 solutions (n=10 for each solution, i.e., two modified UBBC assays per patient) for the carborane-d cyanocobalamin and carborane-b cyanocobalamin was 35.75% and 92.93% respectively, and 98.21% for DAPC.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I

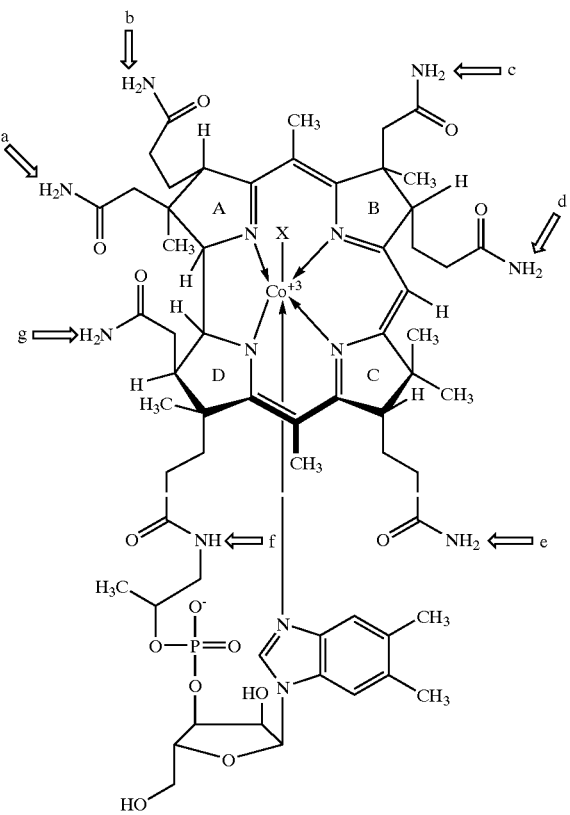

linked to a molecule comprising B-10, wherein X is CN, OH, CH$_3$, adenosyl or a molecule comprising B-10 and optionally linked to a linker comprising a detectable radionuclide or a therapeutic radionuclide; or a pharmaceutically acceptable salt thereof.

2. The compound of claim 1, wherein the molecule comprising B-10 is directly linked to the 6-position of the compound of formula I or is directly linked to the b, d or e-carboxamide group of the compound of formula I.

3. The compound of claim 1, wherein the molecule comprising B-10 is linked by a linker to the 6-position of the compound of formula I or is linked by a linker to the b, d or e-carboxamide group of the compound of formula I.

4. The compound of claim 1, wherein the molecule comprising B-10 is linked to the b-carboxamide group of the compound of formula I.

5. The compound of claim 1, wherein the molecule comprising B-10 is linked to the d-carboxamide group of the compound of formula I.

6. The compound of claim 1, wherein the molecule comprising B-10 is linked to the e-carboxamide group of the compound of formula I.

7. The compound of claim 1, wherein the molecule comprising B-10 is linked to the b-carboxamide group and a second molecule comprising B-10 is linked to the d-carboxamide group of the compound of formula I.

8. The compound of claim 1, wherein molecule comprising B-10 is linked to the 6-position of the compound of formula I.

9. The compound of claim 1, wherein the molecule comprising B-10 contains 1 to about 20 boron atoms, inclusive.

10. The compound of claim 1, wherein the molecule comprising B-10 is an amino acid, a carbohydrate, a nucleoside or a carborane.

11. The compound of claim 1, wherein the molecule comprising B-10 is o-carborane, m-carborane or p-carborane.

12. The compound of claim 1, wherein the molecule comprising B-10 is o-carborane.

13. The compound of claim 3, wherein at least one linker is of the formula W—A—Q wherein A is $(C_1-C_6)$alkyl, $(C_2-C_6)$alkenyl, $(C_2-C_6)$alkynyl, $(C_3-C_8)$cycloalkyl, or $(C_6-C_{10})$aryl, wherein W and Q are each independently —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or $(C_1-C_6)$alkyl.

14. The compound of claim 13, wherein W is $NH_2$ or COOH and Q is $NH_2$ or COOH.

15. The compound of claim 13, wherein A is $(C_1-C_6)$ alkyl.

16. The compound of claim 3, wherein at least one linker is about 5 angstroms to about 50 angstroms, inclusive.

17. The compound of claim 3, wherein at least one linker comprises a therapeutic radionuclide or a diagnostic radionuclide.

18. The compound of claim 17, wherein the therapeutic radionuclide is a metallic radionuclide.

19. The compound of claim 17, wherein the diagnostic radionuclide is a metallic radionuclide.

20. The compound of claim 17, wherein the diagnostic radionuclide is a non-metallic radionuclide.

21. The compound of claim 3, wherein at least one linker is a divalent radical formed from a peptide.

22. The compound of claim 3, wherein at least one linker is a divalent radical formed form an amino acid.

23. The compound of claim 3, wherein at least one linker is poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

24. The compound of claim 1, wherein the compound of formula I is also linked to a linker comprising a detectable radionuclide or a therapeutic radionuclide.

25. A compound of formula I

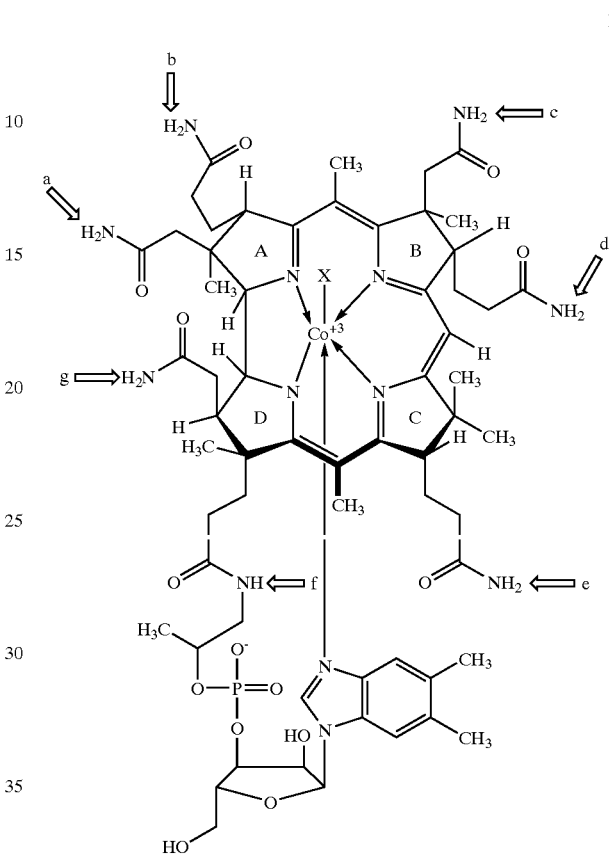

linked to one or more groups of the formula Q—L—W—Det, wherein X is CN, OH, $CH_3$, adenosyl, a molecule comprising B-10 or Q—L—W—Det; wherein Det is a chelating group comprising Gd-157; L is a linker or absent; and W and Q are each independently —N(R)C(=O)—, —C(=O)N(R)—, —OC(=O)—, —C(=O)O—, —O—, —S—; —S(O)—, —S(O)$_2$—, —N(R)—, —C(=O)—, or a direct bond; wherein each R is independently H or $(C_1-C_6)$ alkyl; or a pharmaceutically acceptable salt thereof.

26. The compound of claim 25, wherein the group of the formula Q—L—W—Det is linked to the b-carboxamide group, d-carboxamide group, e-carboxamide group or the 6-position of the compound of formula I.

27. The compound of claim 25, wherein the group of the formula Q—L—W—Det is linked to the b-carboxamide group and a second group of the formula Q—L—W—Det is linked to the d-carboxamide group of the compound of formula I.

28. The compound of claim 25, wherein the group of the formula Q—L—W—Det is between about 20 and about 500 angstroms, inclusive, in length.

29. The compound of claim 25, wherein at least one chelating group is ethylenediaminetetraacetic acid (EDTA); diethylenetriaminepentaacetic acid (DTPA); 1,4,7,10-tetraazacyclododecane-N,N',N'',N'''-tetraacetic acid (DOTA); 1,4,8,11-tetraazacyclotetradecane-N,N',N'',N'''-tetraacetic acid (TETA); 1,4,8, 12-tetraazacyclopentadecane-N,N',N",N'"-tetraacetic acid (15N4); 1,4,7-triazacyclononane-N,N',N"-triacetic acid (9N3); 1,5,9-triazacyclododecane-N,N'N"-triacetic acid (12N3); N-[N-[N-[(benzoylthio)acetyl]glycyl]glycyl] glycine (MAG3); or a cyclohexane-based metal chelator (DCTA) of the formula

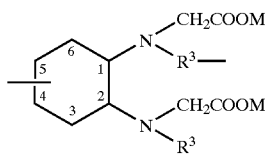

wherein $R^3$ is $(C_1-C_4)$alkyl- or $CH_2CO_2$—, and M is a metal or nonmetal cation.

30. The compound of claim 25, wherein at least one chelating group is diethylenetriaminepentaacetic acid (DTPA) comprising Gd-157.

31. A compound of formula I

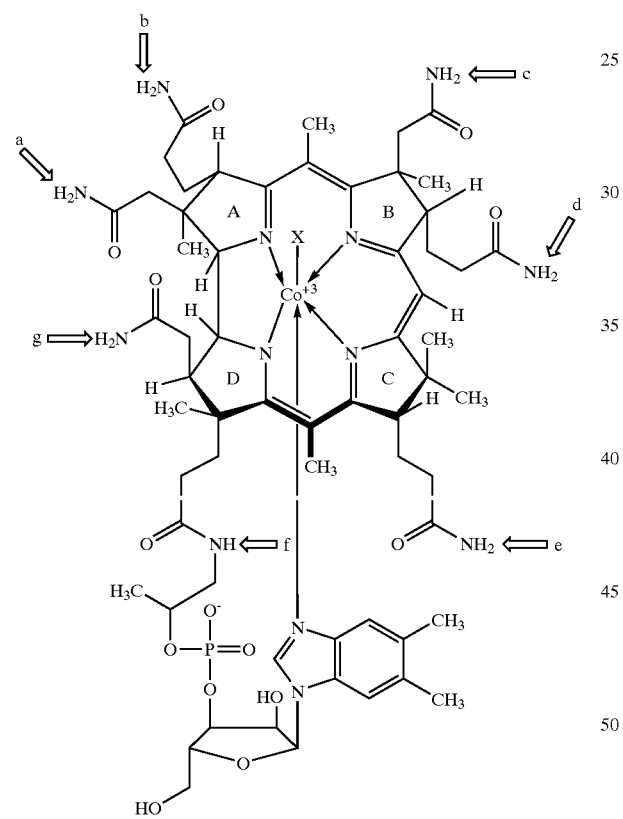

linked to a molecule comprising B-10; wherein the compound of formula I is linked to a group of the formula Q—L—W—Det, wherein X is CN, OH, $CH_3$, adenosyl, a molecule comprising B-10 or Q—L—W—Det; wherein
 a) Det is a chelating group comprising a therapeutic radionuclide or a diagnostic radionuclide;
 b) L is a linker or absent; and
 c) Q and W are each independently —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or $(C_1-C_6)$alkyl;
or a pharmaceutically acceptable salt thereof.

32. The compound of claim 31, wherein at least one of the radionuclides is $Tc^{99m}$, $In^{111}$, $In^{110}$, $Gd^{157}$ or $Y^{86}$.

33. The compound of claim 31, wherein a molecule comprising B-10 is linked to a b-carboxamide group, d-carboxamide group, e-carboxamide group or the 6-position of the compound of formula I.

34. The compound of claim 31, wherein at least one chelating group is ethylenediaminetetaacetic acid (EDTA); diethylenetriaminepentaacetic acid (DTPA); 1,4,7,10-tetraazacyclododecane-N,N',N",N'"-tetraacetic acid (DOTA); 1,4,8,11-tetraazacyclotetradecane-N,N',N",N'"-tetraacetic acid (TETA); 1,4,8,12-tetraazacyclopentadecane-N,N',N",N'"-tetraacetic acid (15N4); 1,4,7-triazacyclononane-N,N',N"-triacetic acid (9N3); 1,5,9-triazacyclododecane-N,N',N"-triacetic acid (12N3); N-[N-[N-[(benzoylthio)acetyl]glycyl]glycyl]glycine (MAG3); or a cyclohexane-based metal chelator (DCTA) of the formula

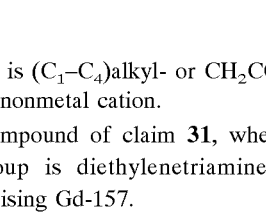

wherein $R^3$ is $(C_1-C_4)$alkyl- or $CH_2CO_2$—, and M is a metal or nonmetal cation.

35. The compound of claim 31, wherein at least one chelating group is diethylenetriaminepentaacetic acid DTPA) comprising Gd-157.

36. The compound of claim 31, wherein the molecule comprising B-10 contains 1 to about 20 boron atoms, inclusive.

37. The compound of claim 31, wherein the molecule comprising B-10 is an amino acid, a carbohydrate, a nucleoside or a carborane.

38. The compound of claim 31, wherein the molecule comprising B-10 is o-nido-carborane, m-nido-carborane or p-nido-carborane.

39. The compound of claim 31, wherein the molecule comprising B-10 is o-carborane.

40. The compound of claim 31, wherein the molecule comprising B-10 is directly linked to the 6-position or to the b, d or e-carboxamide group of the compound of formula I.

41. The compound of claim 31, wherein the compound of formula I is linked to the molecule comprising B-10 through a linker.

42. The compound of claim 41, wherein the linker comprises a non-metallic radionuclide.

43. The compound of claim 41, wherein the linker is about 5 angstroms to about 50 angstroms, inclusive.

44. A compound of formula I

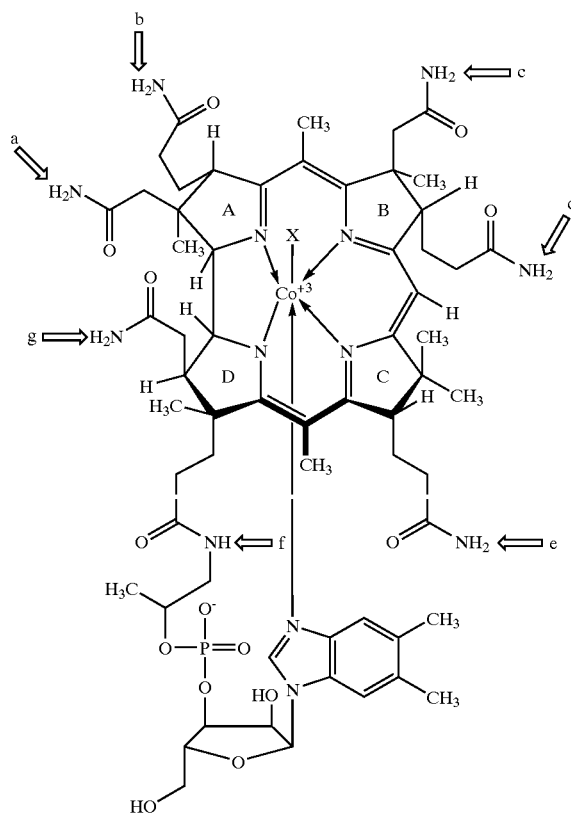

I linked to a molecule comprising B-10, wherein X is CN, OH, $CH_3$, adenosyl or a molecule comprising B-10 comprising at least one detectable radionuclide or a therapeutic radionuclide; or a pharmaceutically acceptable salt thereof.

45. The compound of claim 44, wherein the detectable radionuclide is a non-metallic radionuclide.

46. The compound of claim 45, wherein the non-metallic radionuclide is Carbon-11, Fluorine-18, Bromine-76, Iodine-123 or Iodine-124.

47. The compound of claim 44, wherein the detectable radionuclide is directly linked to the compound of formula I.

48. The compound of claim 44, wherein the detectable radionuclide is linked by a linker to the compound of formula I.

49. The compound of claim 48, wherein the linker is of the formula W—A wherein A is $(C_1-C_6)$alkyl, $(C_2-C_6)$ alkenyl, $(C_2-C_6)$alknyl, $(C_3-C_8)$cycloalkyl, or $(C_6-C_{10})$ aryl, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or $(C_1-C_6)$alkyl, and wherein A is substituted with one or more non-metallic radionuclides.

50. The compound of claim 48, wherein the linker is about 5 angstroms to about 50 angstroms, inclusive.

51. The compound of claim 48, wherein the linker is a divalent peptide or amino acid.

52. The compound of claim 48, wherein the linker is poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

53. The compound of claim 48, wherein the linker is linked to the deposition of the compound of formula I or is linked to the a b-, d- or e-carboxamide group of the compound of formula I.

54. A compound of formula I

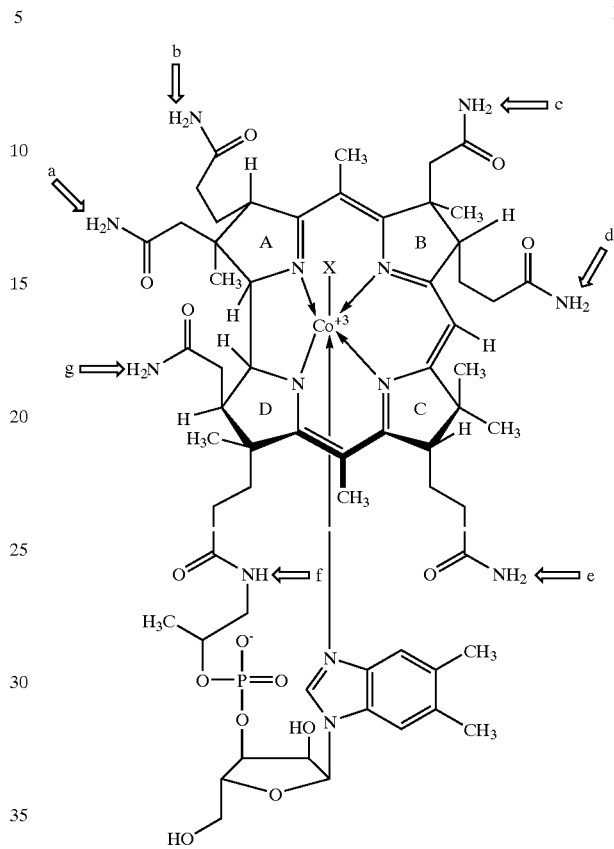

I linked
1) to a molecule comprising B-10 or a chelating group comprising Gd-157; and
2) to at least one molecule of the formula Q—L—W—Det, wherein X is CN, OH, $CH_3$, adenosyl, a molecule comprising B-10 or Q—L—W—Det; wherein each Det is independently a chelating group comprising a metallic radionuclide; each L is independently a linker or absent; and each W and Q are each independently —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or $(C_1-C_6)$alkyl;
or a pharmaceutically acceptable salt thereof.

55. The compound of claim 1 or 44, wherein the compound of formula I is also linked to a group comprising Gd-157.

56. The compound of claim 55, wherein the group comprising Gd-157 has the formula Q—L—W—Det, wherein X is CN, OH, $CH_3$, adenosyl, a molecule comprising B-10or Q—L—W—Det; wherein Det is a chelating group comprising Gd-157; L is a linker or absent; and W and Q are each independently —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or $(C_1-C_6)$alkyl.

57. A composition comprising a compound of any one of claims 1–56 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 6,806,363 B1 | Page 1 of 1 |
| APPLICATION NO. | : 09/690197 | |
| DATED | : October 19, 2004 | |
| INVENTOR(S) | : Douglas A. Collins and Henricus P. C. Hogenkamp | |

It is certified that error appears in the above-identified patent and that said Letters Patent is hereby corrected as shown below:

In claims 1, 25, 31, 44, and 54, please delete the structure for Formula 1, and insert therefor.

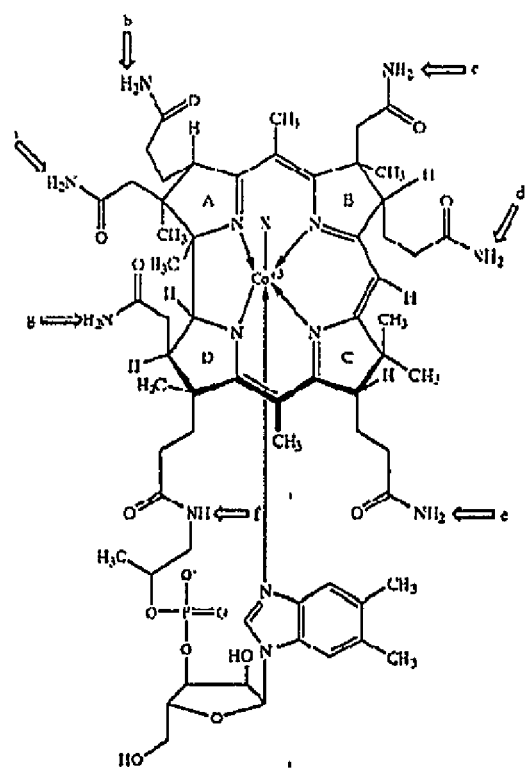

Signed and Sealed this

Twenty-ninth Day of May, 2007

JON W. DUDAS
*Director of the United States Patent and Trademark Office*